United States Patent
Lee et al.

(10) Patent No.: US 10,377,894 B2
(45) Date of Patent: *Aug. 13, 2019

(54) BLOCK COPOLYMER

(71) Applicant: LG Chem, Ltd., Seoul (KR)

(72) Inventors: Jeong Kyu Lee, Daejeon (KR); Je Gwon Lee, Daejeon (KR); In Young Song, Daejeon (KR); Sung Joon Oh, Daejeon (KR); Yeon Joo Kang, Daejeon (KR); Sung Soo Yoon, Daejeon (KR); Jung Keun Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/515,812

(22) PCT Filed: Sep. 30, 2015

(86) PCT No.: PCT/KR2015/010334
§ 371 (c)(1),
(2) Date: Mar. 30, 2017

(87) PCT Pub. No.: WO2016/053010
PCT Pub. Date: Apr. 7, 2016

(65) Prior Publication Data
US 2017/0306074 A1    Oct. 26, 2017

(30) Foreign Application Priority Data

Sep. 30, 2014 (KR) .................. 10-2014-0131964
Dec. 8, 2014 (KR) .................. 10-2014-0175400
(Continued)

(51) Int. Cl.
*C08L 53/00* (2006.01)
*C08G 61/12* (2006.01)
(Continued)

(52) U.S. Cl.
CPC ............ *C08L 53/005* (2013.01); *B05D 1/005* (2013.01); *B05D 3/007* (2013.01);
(Continued)

(58) Field of Classification Search
CPC .. C08F 220/30; C08F 220/301; C08F 220/22; C08F 293/005
See application file for complete search history.

(56) References Cited

U.S. PATENT DOCUMENTS 3,976,672 A    8/1976    Strunk et al.
5,115,056 A    5/1992    Mueller et al.
(Continued)

FOREIGN PATENT DOCUMENTS

CN    1333790 A    1/2002
CN    1337974 A    2/2002
(Continued)

OTHER PUBLICATIONS

Riedel, M.; Stadermann, J.; Komber, H.; Simon, F.; Voit, B. Eur. Polym. J. 2011, 47, 675-684. (Year: 2011).*
(Continued)

*Primary Examiner* — Rip A Lee
(74) *Attorney, Agent, or Firm* — Lerner, David, Littenberg, Krumholz & Mentlik, LLP

(57) ABSTRACT

The present application relates to a block copolymer and its use. The present application can provides a block copolymer that has an excellent self assembling property or phase separation property and therefore can be used in various applications and its use.

26 Claims, 12 Drawing Sheets

(30) Foreign Application Priority Data

| Date | Country | Number |
|---|---|---|
| Dec. 8, 2014 | (KR) | 10-2014-0175401 |
| Dec. 8, 2014 | (KR) | 10-2014-0175402 |
| Dec. 8, 2014 | (KR) | 10-2014-0175406 |
| Dec. 8, 2014 | (KR) | 10-2014-0175407 |
| Dec. 8, 2014 | (KR) | 10-2014-0175410 |
| Dec. 8, 2014 | (KR) | 10-2014-0175411 |
| Dec. 8, 2014 | (KR) | 10-2014-0175412 |
| Dec. 8, 2014 | (KR) | 10-2014-0175413 |
| Dec. 8, 2014 | (KR) | 10-2014-0175414 |
| Dec. 8, 2014 | (KR) | 10-2014-0175415 |
| Jun. 4, 2015 | (KR) | 10-2015-0079488 |

(51) Int. Cl.

| | |
|---|---|
| H01L 21/3105 | (2006.01) |
| G03F 7/16 | (2006.01) |
| H01L 21/027 | (2006.01) |
| C08F 212/08 | (2006.01) |
| C08F 216/12 | (2006.01) |
| C08F 220/10 | (2006.01) |
| C08F 220/26 | (2006.01) |
| C08F 220/30 | (2006.01) |
| C08J 5/18 | (2006.01) |
| B05D 1/00 | (2006.01) |
| B05D 3/00 | (2006.01) |
| C08F 293/00 | (2006.01) |
| C09D 153/00 | (2006.01) |
| G03F 7/09 | (2006.01) |
| G03F 7/004 | (2006.01) |
| G03F 7/039 | (2006.01) |
| G03F 7/20 | (2006.01) |
| C08F 32/06 | (2006.01) |
| C08F 299/02 | (2006.01) |
| C08G 61/08 | (2006.01) |
| C08F 2/14 | (2006.01) |
| C08J 7/12 | (2006.01) |
| G03F 7/00 | (2006.01) |
| G03F 7/30 | (2006.01) |
| C08L 53/02 | (2006.01) |
| B81C 1/00 | (2006.01) |
| B82Y 40/00 | (2011.01) |

(52) U.S. Cl.
CPC ............ *B81C 1/00428* (2013.01); *C08F 2/14* (2013.01); *C08F 32/06* (2013.01); *C08F 212/08* (2013.01); *C08F 216/12* (2013.01); *C08F 220/10* (2013.01); *C08F 220/26* (2013.01); *C08F 220/30* (2013.01); *C08F 293/00* (2013.01); *C08F 293/005* (2013.01); *C08F 299/024* (2013.01); *C08G 61/08* (2013.01); *C08G 61/12* (2013.01); *C08J 5/18* (2013.01); *C08J 7/123* (2013.01); *C08L 53/00* (2013.01); *C08L 53/02* (2013.01); *C09D 153/00* (2013.01); *G03F 7/0002* (2013.01); *G03F 7/0046* (2013.01); *G03F 7/039* (2013.01); *G03F 7/091* (2013.01); *G03F 7/16* (2013.01); *G03F 7/162* (2013.01); *G03F 7/165* (2013.01); *G03F 7/2004* (2013.01); *G03F 7/30* (2013.01); *H01L 21/0273* (2013.01); *H01L 21/31055* (2013.01); *H01L 21/31056* (2013.01); *H01L 21/31058* (2013.01); *B81C 2201/0149* (2013.01); *B82Y 40/00* (2013.01); *C01P 2002/70* (2013.01); *C07B 2200/00* (2013.01); *C08F 2220/301* (2013.01); *C08F 2438/03* (2013.01); *C08G 2261/1424* (2013.01); *C08G 2261/1426* (2013.01); *C08G 2261/332* (2013.01); *C08G 2261/3324* (2013.01); *C08G 2261/40* (2013.01); *C08G 2261/418* (2013.01); *C08J 2353/00* (2013.01)

(56) References Cited

U.S. PATENT DOCUMENTS

| | | | |
|---|---|---|---|
| 5,202,402 A | 4/1993 | Funaki et al. | |
| 5,234,604 A | 8/1993 | Liao et al. | |
| 5,391,626 A | 2/1995 | Machida et al. | |
| 5,418,290 A | 5/1995 | Machida et al. | |
| 5,546,282 A | 8/1996 | Hill et al. | |
| 5,554,695 A | 9/1996 | Vlachida et al. | |
| 5,728,431 A | 3/1998 | Bergbreiter et al. | |
| 6,025,437 A | 2/2000 | Hirahara et al. | |
| 6,314,225 B1 | 11/2001 | Wang | |
| 6,531,547 B1 | 3/2003 | Visger et al. | |
| 6,953,649 B2 | 10/2005 | Prat et al. | |
| 7,538,159 B2 | 5/2009 | Wang et al. | |
| 8,163,189 B2 | 4/2012 | Iyoda et al. | |
| 8,211,737 B2 | 7/2012 | Russell et al. | |
| 8,791,042 B2 | 7/2014 | Ronan et al. | |
| 9,177,818 B2 * | 11/2015 | Hieno | H01L 21/3081 |
| 9,495,991 B2 | 11/2016 | Han et al. | |
| 2003/0143343 A1 | 7/2003 | Kawabata et al. | |
| 2004/0049836 A1 | 3/2004 | Ashraf et al. | |
| 2004/0110856 A1 | 6/2004 | Young et al. | |
| 2004/0143032 A1 | 7/2004 | Auschra et al. | |
| 2004/0242787 A1 | 12/2004 | Chun et al. | |
| 2006/0166033 A1 | 7/2006 | Poetsch et al. | |
| 2007/0142559 A1 | 6/2007 | Wang et al. | |
| 2007/0166648 A1 | 7/2007 | Ponoth et al. | |
| 2007/0219338 A1 | 9/2007 | Takeda et al. | |
| 2008/0105854 A1 | 5/2008 | Huh et al. | |
| 2008/0193658 A1 | 8/2008 | Millward | |
| 2008/0213556 A1 | 9/2008 | Cha et al. | |
| 2008/0286333 A1 | 11/2008 | Kangas et al. | |
| 2008/0311402 A1 | 12/2008 | Jung et al. | |
| 2009/0114108 A1 | 5/2009 | Oya et al. | |
| 2009/0240001 A1 | 9/2009 | Regner | |
| 2009/0253867 A1 | 10/2009 | Takahashi et al. | |
| 2009/0306295 A1 | 12/2009 | Mays et al. | |
| 2010/0086801 A1 | 4/2010 | Russell et al. | |
| 2010/0098876 A1 | 4/2010 | Hanson | |
| 2010/0102415 A1 | 4/2010 | Millward et al. | |
| 2010/0120985 A1 | 5/2010 | Konishi et al. | |
| 2010/0155988 A1 | 6/2010 | Keil et al. | |
| 2010/0206057 A1 | 8/2010 | Batchelder et al. | |
| 2010/0210742 A1 | 8/2010 | Iyoda et al. | |
| 2010/0216312 A1 | 8/2010 | Yamamoto et al. | |
| 2010/0266957 A1 | 10/2010 | Harada et al. | |
| 2010/0285276 A1 | 11/2010 | Kim et al. | |
| 2010/0286351 A1 | 11/2010 | Yoshida et al. | |
| 2010/0305230 A1 | 12/2010 | Li et al. | |
| 2011/0186544 A1 | 8/2011 | Endou et al. | |
| 2011/0253946 A1 | 10/2011 | Huh et al. | |
| 2011/0294070 A1 * | 12/2011 | Hatakeyama | C08F 20/26 430/285.1 |
| 2012/0052446 A1 | 3/2012 | Jaycox et al. | |
| 2012/0116024 A1 | 5/2012 | Iyoda et al. | |
| 2012/0214094 A1 | 8/2012 | Mikoshiba et al. | |
| 2012/0248945 A1 * | 10/2012 | Koo | H01L 41/0986 310/365 |
| 2013/0078576 A1 | 3/2013 | Wu et al. | |
| 2013/0183828 A1 | 7/2013 | Nakamura et al. | |
| 2013/0189504 A1 | 7/2013 | Nealey et al. | |
| 2013/0209693 A1 | 8/2013 | Vogel et al. | |
| 2013/0209755 A1 | 8/2013 | Hustad et al. | |
| 2013/0248488 A1 | 9/2013 | Han et al. | |
| 2013/0284698 A1 | 10/2013 | Ogihara | |
| 2013/0306594 A1 | 11/2013 | Hustad et al. | |
| 2014/0011916 A1 | 1/2014 | Lee et al. | |
| 2014/0127456 A1 | 5/2014 | Regner | |
| 2014/0141375 A1 | 5/2014 | Cho et al. | |
| 2014/0238954 A1 | 8/2014 | Matsumiya et al. | |

(56) References Cited

U.S. PATENT DOCUMENTS

| | | | |
|---|---|---|---|
| 2014/0370442 A1 | 12/2014 | Ober et al. | |
| 2015/0064630 A1 | 3/2015 | Wuister et al. | |
| 2015/0085042 A1 | 3/2015 | Keoshkerian et al. | |
| 2015/0197663 A1 | 7/2015 | Mizutani et al. | |
| 2015/0228298 A1 | 8/2015 | Han et al. | |
| 2016/0204653 A1 | 7/2016 | Lee | |
| 2016/0257838 A1 | 9/2016 | Senzaki et al. | |
| 2016/0280823 A1* | 9/2016 | Kim | C08F 210/18 |
| 2016/0280831 A1* | 9/2016 | Park | C08F 293/005 |
| 2016/0280832 A1* | 9/2016 | Kim | C07C 43/215 |
| 2016/0280833 A1 | 9/2016 | Lee et al. | |
| 2016/0280834 A1* | 9/2016 | Kim | C08F 293/005 |
| 2016/0280835 A1* | 9/2016 | Lee | C07C 43/215 |
| 2016/0304653 A1* | 10/2016 | Kim | C07C 43/215 |
| 2016/0304654 A1* | 10/2016 | Lee | C07C 43/215 |
| 2016/0304655 A1* | 10/2016 | Lee | C07C 43/215 |
| 2016/0311958 A1* | 10/2016 | Kim | C07C 43/215 |
| 2016/0311959 A1* | 10/2016 | Lee | C07C 43/215 |
| 2016/0311960 A1 | 10/2016 | Lee et al. | |
| 2016/0333221 A1 | 11/2016 | Mumtaz et al. | |
| 2017/0008992 A1* | 1/2017 | Lee | C07C 43/215 |
| 2017/0058071 A1* | 3/2017 | Lee | C07C 43/215 |
| 2017/0210938 A1* | 7/2017 | Ku | H01L 21/31056 |
| 2017/0219922 A1* | 8/2017 | Ku | H01L 21/31056 |
| 2017/0226235 A1 | 8/2017 | Park et al. | |
| 2017/0226258 A1 | 8/2017 | Lee et al. | |
| 2017/0226260 A1 | 8/2017 | Lee et al. | |
| 2017/0226261 A1 | 8/2017 | Lee et al. | |
| 2017/0247492 A1 | 8/2017 | Choi et al. | |
| 2017/0306074 A1 | 10/2017 | Lee et al. | |
| 2017/0306139 A1* | 10/2017 | Kim | H01L 21/31056 |
| 2017/0313869 A1* | 11/2017 | Lee | H01L 21/31056 |
| 2018/0170023 A1 | 6/2018 | Park et al. | |

FOREIGN PATENT DOCUMENTS

| | | | | |
|---|---|---|---|---|
| CN | 101215362 A | 7/2008 | | |
| CN | 101443371 A | 5/2009 | | |
| CN | 101492520 A | 7/2009 | | |
| CN | 101578232 A | 11/2009 | | |
| CN | 101688047 A | 3/2010 | | |
| CN | 101799626 A | 8/2010 | | |
| CN | 101977839 A | 2/2011 | | |
| CN | 102172491 A | 9/2011 | | |
| CN | 102439076 A | 5/2012 | | |
| CN | 102967918 A | 3/2013 | | |
| CN | 103025827 A | 4/2013 | | |
| CN | 103180783 A | 6/2013 | | |
| CN | 103289285 A | 9/2013 | | |
| CN | 103562245 A | 2/2014 | | |
| CN | 103797066 A | 5/2014 | | |
| CN | 105899556 A | 8/2016 | | |
| CN | 105899557 A | 8/2016 | | |
| CN | 105899559 A | 8/2016 | | |
| CN | 105899560 A | 8/2016 | | |
| CN | 105934454 A | 9/2016 | | |
| CN | 105934456 A | 9/2016 | | |
| CN | 105960422 A | 9/2016 | | |
| CN | 105980342 A | 9/2016 | | |
| CN | 106459326 A | 2/2017 | | |
| CN | 107075052 A | 8/2017 | | |
| EP | 1141056 B1 | 8/2010 | | |
| EP | 2781550 A1 | 9/2014 | | |
| EP | 3078654 A1 | 10/2016 | | |
| EP | 3078691 B1 | 10/2016 | | |
| EP | 3078692 A1 | 10/2016 | | |
| EP | 3078694 A1 | 10/2016 | | |
| EP | 3203497 A1 | 8/2017 | | |
| EP | 3214102 A1 | 9/2017 | | |
| EP | 3225641 A1 | 10/2017 | | |
| GB | 898065 A | 6/1962 | | |
| JP | 01260360 A | 10/1989 | | |
| JP | H01260360 A | 10/1989 | | |
| JP | H5320281 A | 12/1993 | | |
| JP | H0665333 A | 3/1994 | | |
| JP | H10237143 A | 9/1998 | | |
| JP | H10245427 A | 9/1998 | | |
| JP | H1143523 A | 2/1999 | | |
| JP | 2000053734 A | 2/2000 | | |
| JP | 2000281737 A | 10/2000 | | |
| JP | 2000285751 A | 10/2000 | | |
| JP | 3121116 B2 | 12/2000 | | |
| JP | 2001513125 A | 8/2001 | | |
| JP | 2001294617 A | 10/2001 | | |
| JP | 2002145973 A | 5/2002 | | |
| JP | 2003536105 A | 12/2003 | | |
| JP | 2004026688 A | 1/2004 | | |
| JP | 2004323773 A | 11/2004 | | |
| JP | 2005015508 A | 1/2005 | | |
| JP | 2005097442 A | 4/2005 | | |
| JP | 2005148205 A | 6/2005 | | |
| JP | 2005530030 A | 10/2005 | | |
| JP | 2005531618 A | 10/2005 | | |
| JP | 2007070453 A | 3/2007 | | |
| JP | 2007077292 A | 3/2007 | | |
| JP | 2007246600 A | 9/2007 | | |
| JP | 200855579 A | 3/2008 | | |
| JP | 2009057519 A | 3/2009 | | |
| JP | 200986354 A | 4/2009 | | |
| JP | 2009203439 A | 9/2009 | | |
| JP | 2010507803 A | 3/2010 | | |
| JP | 2010-116466 A | * | 5/2010 | C08L 55/00 |
| JP | 2010115832 A | 5/2010 | | |
| JP | 2010116466 A | 5/2010 | | |
| JP | 2010145158 A | 7/2010 | | |
| JP | 2010202723 | 9/2010 | | |
| JP | 2010275349 A | 12/2010 | | |
| JP | 4625901 B2 | 2/2011 | | |
| JP | 2012001787 A | 1/2012 | | |
| JP | 2012012577 A | 1/2012 | | |
| JP | 2012036078 A | 2/2012 | | |
| JP | 2012093699 A | 5/2012 | | |
| JP | 2012174984 A | 9/2012 | | |
| JP | 201368882 A | 4/2013 | | |
| JP | 2013512323 A | 4/2013 | | |
| JP | 2013514449 A | 4/2013 | | |
| JP | 2013121430 A | 6/2013 | | |
| JP | 2013219334 A | 10/2013 | | |
| JP | 2013232501 A | 11/2013 | | |
| JP | 201412807 A | 1/2014 | | |
| JP | 2014070154 A | 4/2014 | | |
| JP | 2014102503 A | 6/2014 | | |
| JP | 2014162054 A | 9/2014 | | |
| JP | 2015000896 A | 1/2015 | | |
| JP | 2016539239 A | 12/2016 | | |
| JP | 2016540863 A | 12/2016 | | |
| JP | 2017502116 A | 1/2017 | | |
| JP | 2017505356 A | 2/2017 | | |
| JP | 2017530236 A | 10/2017 | | |
| JP | 2017530238 A | 10/2017 | | |
| JP | 2017533302 A | 11/2017 | | |
| KR | 20010101356 | 11/2001 | | |
| KR | 100622353 B1 | 9/2006 | | |
| KR | 20090015742 A | 2/2009 | | |
| KR | 100935863 B1 | 1/2010 | | |
| KR | 20100033962 A | 3/2010 | | |
| KR | 20100070380 A | 6/2010 | | |
| KR | 20100123920 A | 11/2010 | | |
| KR | 20110018678 A | 2/2011 | | |
| KR | 20110086834 A | 8/2011 | | |
| KR | 20110097707 A | 8/2011 | | |
| KR | 20110102998 A | 9/2011 | | |
| KR | 20110112501 A | 10/2011 | | |
| KR | 101102680 B1 | 1/2012 | | |
| KR | 20120119998 A | 11/2012 | | |
| KR | 20130094264 A | 8/2013 | | |
| KR | 20130113596 A | 10/2013 | | |
| KR | 20130128346 A | 11/2013 | | |
| KR | 20140063790 A | 5/2014 | | |
| KR | 20150066488 A | 6/2015 | | |
| KR | 20150067065 A | 6/2015 | | |
| KR | 20150067069 A | 6/2015 | | |
| KR | 20150067070 A | 6/2015 | | |
| KR | 20160038705 | 4/2016 | | |

(56) References Cited

FOREIGN PATENT DOCUMENTS

| | | |
|---|---|---|
| TW | 201323461 A | 6/2013 |
| TW | 201428046 A | 7/2014 |
| TW | 201536823 A | 10/2015 |
| TW | 201538548 A | 10/2015 |
| WO | 9837136 A1 | 8/1998 |
| WO | 2007055371 A1 | 5/2007 |
| WO | 2012144735 A2 | 10/2012 |
| WO | 2013069544 A1 | 5/2013 |
| WO | 2013120051 A1 | 8/2013 |
| WO | 2013158527 A1 | 10/2013 |
| WO | 2014050905 A1 | 4/2014 |
| WO | 2014090178 A1 | 6/2014 |
| WO | 2014124795 A1 | 8/2014 |
| WO | 2015084121 A1 | 6/2015 |
| WO | 2015084122 A1 | 6/2015 |
| WO | 2015084123 A1 | 6/2015 |
| WO | 2015084124 A1 | 6/2015 |
| WO | 2015084125 A1 | 6/2015 |
| WO | 2015084126 A1 | 6/2015 |
| WO | 2015084127 A1 | 6/2015 |
| WO | 2015087005 A1 | 6/2015 |
| WO | 2016052994 A1 | 4/2016 |
| WO | 2016052999 A1 | 4/2016 |
| WO | 2016053005 A1 | 4/2016 |
| WO | 2016053007 A1 | 4/2016 |
| WO | 2016053011 A1 | 4/2016 |

OTHER PUBLICATIONS

Nilles, K.; Theato, P. J. Polymer Science: Part A: Polymer Chemistry 2009, 47, 1696-1705. (Year: 2009).*

Borkar, S.; Jankova, K.; Siesler, H.W.; Hvilstead, S. Macromolecules 2001, 37, 788-794 (Year: 2001).*

Anonymous., "Solid surface energy data (SFE) for common polymers", surface-tension.de, Feb. 2017, Retreived from the Internet: URL:http://www.surface-tension.de/solid-surface-energy.htm, XP002775246.

Cummins et al., "Solvothermal Vapor Annealing of Lamellar Poly-(styrene)-block-poly(D,L-lactide) Block Copolymer Thin Films for Directed Self-Assembly Application", ACS Applied Materials & Interfaces, Mar. 2016, vol. 8, No. 12, pp. 58295-8304, XP055419698.

Extended European Search Report for Application No. EP14867808.9 dated Nov. 10, 2017.

Extended European Search Report for Application No. EP14868022.6 dated Nov. 6, 2017.

Extended European Search Report for Application No. EP14868320.4 dated Nov. 20, 2017.

Extended European Search Report for Application No. EP14868480.6 dated Nov. 2, 2017.

Hvilsted et al., "Novel Fluorinated Polymer Materials Based on 2,3,5,6-Tetrafluoro-4-methoxyystyrene" In: "Advances in Controlled/Living Radical Polymerization", American Chemical Society, Jun. 26, 2003, vol. 854, pp. 236-249, XP055421064.

Mahajan et al., "Synthesis and Characterization of Amphiphilic Poly(ethylene oxide)-block-poly(hexylmethacrylate Copolymers", Macromolecular Chemistry and Physics, Wiley-Vch Verlag, Weinheim, DE, Jan. 2003, vol. 204, pp. 1047-1055, XP003030406.

Pochan et al., "Morphologies of microphase-seperated conformationally asymmetric diblock copolymers", Journal of Polymer Science Part B: Polymer Physics, Nov. 2017, vol. 35, No. 16, pp. 2629-2643, XP055417266.

Zhuang et al., "Synthesis of A-B type block copolymers using 1-phenylethyl dithiobenzoate as Reversible Addition-Fragmentation Chain Transfer agent", Database CA [online], Chemical Abstracts Service, Columbus, OH, XP002775247.

Chinese Search Report for Application No. 201480072759.9 dated Jan. 24, 2018.

Chinese Search Report for CN Application No. 201480071920.0, dated May 4, 2018.

Chinese Search Report for CN Application No. 201480072800.2, dated Apr. 10, 2018.

Chinese Search Report for CN Application No. 201480074045.1, dated Apr. 11, 2018.

Extended European Seach Report including Written Opinion for EP Application No. 15847574.9, dated May 3, 2018.

Extended European Search Report including Written Opinion for EP Application No. 15845928.9, dated May 2, 2018.

Extended European Search Report including Written Opinion for EP Application No. 15847598.8, dated May 11, 2018.

Extended European Search Report including Written Opinion for EP15845720.0 dated May 4, 2018.

Extended European Search Report with Written Opinion for EP158468322 dated May 3, 2018.

Funk, L. et al., "Novel Amphiphilic Styrene-Based Block Copolymers for Induced Surface Reconstruction," Macromolecular Chemistry and Physics, vol. 209, No. 1, Jan. 4, 2008, pp. 52-63, XP055382259, DE, ISSN: 1022-1352, DOI: 10.1002/macp.200700312.

Haeng-Dong Koh et al., "Location-controlled parallel and vertical orientation by dewetting-induced block copolymer directed self-assembly," Journal of Materials Chemistry C: Materials for Optical and Electronic Devices, vol. 1, No. 25, Jan. 1, 2013, pp. 4020-4024 XP055469744.

Ma J et al., "Synthesis and Solution-State Assembly or Buld State Thiol-ene Crosslinking of Pyrrolidinone- and Alkene-Functionalized Amphiphilic Block Fluorocopoplymers: From Functional Nanoparticles to Anti-Fouling Coatings", Australian Journal of Chemistry: An International Journal for Chemical Sci, Jan. 1, 2010, pp. 1159-1163, vol. 63, No. 8,C S I R O Publishing, Australia.

Mori H. et al., "Synthesis and Surface Characterization of Hydrophilic-Hydrophobic Block Copolymers Containing Poly(2,3-dihydroxypropyl methacrylate)," Macromolecules, American Chemical Society, US, vol. 27, No. 15, Jul. 18, 1994, pp. 4093-9297; XP000456650, DOI: 10.2021/MA00093A010.

Segalman R.A. et al., "Graphoepitaxy of Spherical Domain Block Copolymer Films," Advanced Materials, Wiley—VCH Verlag GmbH & Co. KGAA, DE, vol. 13, No. 15, Aug. 3, 2001, pp. 1152-1155; XP001129643, ISSN: 0935-9648, DOI: 10.1002/1521-4095(200108)13:15<1152: AID-A DMA1152>3.0.CO; 2-5.

Database CA [Online] Chemical Abstracts Service Ohi0 US; Zou, Yue: "Fluorosurfactant capable of preventing unevenness in photoresist coating and its preparation by anionic polymerization", XP002771143 retrieved from STN Database accession No. 2011:1148166 * abstract * & CN 102 172 491 A (Jiangsu Johnny Material Technology Co Ltd) Sep. 7, 2011 (Sep. 7, 2011) Columbus, No. 2011:1148166.

European Search Report for Application No. EP14867501 dated Jul. 14, 2017.

Kago K et al: "X-ray reflectivity of polymer assembly at air-water interface" Supramolecular Science Butterworth-Heinemann Oxford GB vol. 5 No. 3-4, Jul. 1, 1998 (Jul. 1, 1998)pp. 349-355 XP027388373 ISSN: 0968-5677 [retrieved on Jul. 1, 1998] * abstract *.

Lutz Funk et al: "Novel Amphiphilic Styrene-Based Block Copolymers for Induced Surface Reconstruction". Macromolecular Chemistry and Physics., vol. 209, No. 1, Jan. 4, 2008 (Jan. 4, 2008), XP055382259 DE ISSN: 1022-1352 D0I: 10.1002/macp.200700312 * scheme 1, monomers M1, M4 table 2*.

Mori H et al: "Synthesis and Surface Characterization of Hydrophilic-Hydrophobic Block Copolymers Containing Poly(2, 3-Dihydroxypropyl Methacrylate)" Macromolecules American Chemical Society US vol. 27 No. 15 Jul. 18, 1994 (Jul. 18, 1994) pp. 4093-4100 XP000456650 ISSN: 0024-9297 D0I: 10.1021/MA00093A010 * abstract *.

CN Search Report for Application No. 201480071920.0 dated Aug. 2, 2017.

CN Search Report for Application No. CN201480072884.X dated Aug. 3, 2017.

CN Search Report for Application No. CN2014800740447 dated Aug. 1, 2017.

Extended European Search Report for Application No. EP14867273 dated Aug. 10, 2017.

(56) References Cited

OTHER PUBLICATIONS

Mariana Beija et al: "Fluorescence Anisotropy of Hydrophobic Probes in poly(N-decylacrylamide) block-poly(N, N-diethylacrylamide) Block Copolymer Aqueous Solutions: Evidence of Premicellar Aggregates" Journal of Physical Chemistry Part B: Condensed Matter, Materials, Surfaces, Interfaces & Bi0physical, vol. 114, No. 31, Aug. 12, 2010 (Aug. 12, 2010), 9977-9986, XP055394763, US ISSN: 1520-6106, D0I: 10.1021/jp101613y * abstract * * Scheme 1, PDcA11-block-PDEA295; p. 9978 *.
Akiba, Isamu, et al., "Self-Assembly of Amphiphilic Block Copolymers Containing Poly(n-octadecyl acrylate) Block in Aqueous Solution." IOP Conference Series: Materials Science and Engineering, 2010, vol. 14, No. 1, pp. 1-8.
Hua et al. Temperature-induced phase-transitions of methoxyoligo(oxyethylene) styrene-based block copolymers in aqueous solution, Soft Matter, 2013, 9, 8897.
International Search Report from PCT/KR2014/012023, dated Mar. 10, 2015.
International Search Report from PCT/KR2014/012024, dated Mar. 17, 2015.
International Search Report from PCT/KR2014/012025, dated Mar. 17, 2015.
International Search Report from PCT/KR2014/012026, dated Mar. 17, 2015.
International Search Report from PCT/KR2014/012027, dated Mar. 17, 2015.
International Search Report from PCT/KR2014/012028, dated Mar. 17, 2015.
International Search Report from PCT/KR2014/012029, dated Mar. 17, 2015.
International Search Report from PCT/KR2014/012030, dated Mar. 17, 2015.
International Search Report from PCT/KR2014/012031, dated Feb. 12, 2015.
International Search Report from PCT/KR2014/012032, dated Feb. 12, 2015.
International Search Report from PCT/KR2014/012033, dated Feb. 12, 2015.
International Search Report from PCT/KR2014/012034, dated Feb. 12, 2015.
International Search Report from PCT/KR2014/012035, dated Feb. 12, 2015.
International Search Report from PCT/KR2014/012036, dated Mar. 17, 2015.
International Search Report from PCT/KR2015/010313, dated Nov. 23, 2015.
International Search Report from PCT/KR2015/010320, dated Jan. 13, 2016.
International Search Report from PCT/KR2015/010322, dated Jan. 13, 2016.
International Search Report from PCT/KR2015/010323, dated Jan. 13, 2016.
International Search Report from PCT/KR2015/010327, dated Jan. 12, 2016.
International Search Report from PCT/KR2015/010330 dated Jan. 11, 2016.
International Search Report from PCT/KR2015/010332 dated Jan. 13, 2016.
International Search Report from PCT/KR2015/010334, dated Jan. 13, 2016.
International Search Report from PCT/KR2015/010335 dated Jan. 13, 2016.
International Search Report from PCT/KR2015/010338 dated Jan. 14, 2016.
IPO Search Report from Taiwan Application No. 103142745, dated Dec. 14, 2015.
IPO Search Report from Taiwan Application No. 103142777, dated Dec. 15, 2015.
IPO Search Report from Taiwan Application No. 103142780, dated Dec. 15, 2015.
IPO Search Report from Taiwan Application No. 103142784, dated Jan. 27, 2016.
IPO Search Report from Taiwan Application No. 103142786, dated Jan. 11, 2016.
IPO Search Report from Taiwan Application No. 103142790, dated Dec. 15, 2015.
IPO Search Report from Taiwan Application No. 103142794, dated Dec. 15, 2015.
IPO Search Report from Taiwan Application No. 103142798, dated Dec. 16, 2015.
IPO Search Report from Taiwan Application No. 103142805, dated Dec. 11, 2015.
IPO Search Report from Taiwan Application No. 103142955, dated Jan. 15, 2016.
IPO Search Report from Taiwan Application No. 103142956 dated Jan. 20, 2016.
IPO Search Report from Taiwan Application No. 103142963, dated Dec. 10, 2015.
IPO Search Report from Taiwan Application No. 104132186, dated Aug. 18, 2016.
IPO Search Report from Tawain Application No. 103142782, dated Dec. 11, 2015.
Khazimullis et al. "Gel formation in a mixture of a block copolymer and a nematic liquid crystal", Physical Review E 84, 021710 (2011).
Park et al., "Block Copolymer Lithography: Periodic Arrays of~10 11 Holes in 1 Square Centimeter", Science 276, p. 1401-1404, May 30, 1997.
Tenneti et al. "Competition between liquid crystallinity and block copolymer self-assembly in core-shell rod-coil block copolymers", Soft Matter, 2008, 4, 458-461 (2008).
Tenneti et al. Hierarchical Nanostructures of Mesogen Jacketed Bent-Core Liquid Crystalline Block Copolymers, Proceedings Published 2007 by the American Chemical Society.
U.S. Appl. No. 15/101,794, filed Jun. 3, 2016.
U.S. Appl. No. 15/101,812, filed Jun. 3, 2016.
U.S. Appl. No. 15/101,827, filed Jun. 3, 2016.
U.S. Appl. No. 15/101,915, filed Jun. 5, 2016.
U.S. Appl. No. 15/102,089, filed Jun. 6, 2016.
U.S. Appl. No. 15/102,112, filed Jun. 6, 2016.
Chinese Search Report for Application No. 2014800727599 dated Jan. 8, 2018.
Chinese Search Report for Application No. 2014800741401 dated Mar. 9, 2018.
Chinese Search Report for Application No. 201480074156.2 dated Apr. 3, 2018.
Supplementary European Search Report for EP15847157 dated Mar. 21, 2018.
Palacios et al., Constructing Robust and Functional Micropatterns on Polystyrene Surfaces by Using Deep UV Irradiation, American Chemical Society, Langmuir, 29(8) pp. 2756-2763, Feb. 2013.
U.S. Appl. No. 15/102,139, filed Jun. 6, 2016.
U.S. Appl. No. 15/102,149, filed Jun. 6, 2016.
U.S. Appl. No. 15/102,156, filed Jun. 6, 2016.
U.S. Appl. No. 15/173,670, filed Jun. 5, 2016.
U.S. Appl. No. 15/173,671, filed Jun. 5, 2016.
U.S. Appl. No. 15/173,673, filed Jun. 5, 2016.
U.S. Appl. No. 15/173,674, filed Jun. 5, 2016.
U.S. Appl. No. 15/173,676, filed Jun. 5, 2016.
U.S. Appl. No. 15/514,929, filed Mar. 28, 2017.
U.S. Appl. No. 15/514,939, filed Mar. 28, 2017.
U.S. Appl. No. 15/514,959, filed Mar. 28, 2017.
U.S. Appl. No. 15/514,967, filed Mar. 28, 2017.
U.S. Appl. No. 15/515,290, filed Mar. 29, 2017.
U.S. Appl. No. 15/515,293, filed Mar. 29, 2017.
U.S. Appl. No. 15/515,432, filed Mar. 29, 2017.
U.S. Appl. No. 15/515,818, filed Mar. 30, 2017.
U.S. Appl. No. 15/515,821, filed Mar. 30, 2017.
Riedel et al., Synthesis, post-modification and self-assembled thin films of pentafluorostyrene containing block copolymers, European Polymer Journal 47 (2011) 675-684.
Yoshida, E. et al. Polymer Journal vol. 31 (5) pp. 429-434 (1999).
Chinese Search Report for Application No. CN201580059758.5 dated Sep. 5, 2018.

(56) References Cited

OTHER PUBLICATIONS

Chinese Search Report for Application No. CN201580060097.8 dated Sep. 19, 2018.
CN Search Report for Application No. CN201580059710.4. dated Sep. 3, 2018.
Extended European Search Report including Written Opinion for EP Application 15846126.9 dated Sep. 12, 2018.
Kobayashi S, Matsuzawa T, Matsuoka SI, Tajima H, Ishizone T. Living Anionic Polymerizations of 4-(1-Adamantyl) styrene and 3-(4-Vinylphenyl)-1, 1′-biadamantane. Macromolecules. Sep. 5, 2006;39(18):5979-86.
Beng H. Tan et al, "Synthesis and Self-Assembly of pH-Responsive Amphiphilic Poly (dimethylaminoethylmethacrylate)-block-Poly(pentafluorostyrene) Block Copolymer in Aqueous Solution", Macromolecular Rapid Communications, Jun. 17, 2009, vol. 30 (12), pp. 1002-1008.
C.M. Bates et al., "Polymeric Cross-Linked Surface Treatments for Controlling Block Copolymer Orientation in Thin Films", Langmuir Article, American Chemical Society, Jan. 7, 2011, vol. 27, No. 5, pp. 1-7.
Chakrabarty, et al., "Tailor-Made Polyfluoroacrylate and its Block Copolymer by RAFT Polymerization in Miniemulsion; Improved Hydrophobicity in the Core-Shell Block Copolymer", Journal of Colloid and Interface Science, vol. 408, Oct. 2013, pp. 66-74.
Chinese Search Report for CN Application No. 201480074044.7 dated Jun. 7, 2018, completed May 30, 2018.
Extended European Search Report including Written Opinion for Application No. EP15845665.7 dated Jun. 27, 2018.
Frank S. Bates et al., "Block Copolymer Thermodyanmics: Theory and Experiment", Annu. Rev. Phys. Chem., Oct. 1990, vol. 41 (1), pp. 525-557.
G.R. Strobl, "The Physics of Polymers: Concepts for Understanding Their Structures and Behavior", Springer (Abstract Only).
Gregory, et al., "Complex Polymer Architectures via RAFT Polymerization: From Fundamental Process to Extending the Scope Using Click Chemistry and Nature's Building Blocks", Progress in Polymer Science, vol. 37, No. 1, Jan. 2012, pp. 38-105.
Katja Nilles et al., "RAFT Polymerization of Activated 4-Vinylbenzoates"., Journal of Polymer Science: Part A: Polymer Chemistry, Jan. 1, 2009, vol. 47, pp. 1696-1705.
S. Chavda et al., "Synthesis of stimuli responsive PEG47-b-PAA126-b-PSt32 triblock copolymer and its self-assembly in aqueous solutions", European Polymer Journal, Sep. 2012, vol. 49, pp. 209-216.
Sachin Borkar et al., "New Highly Fluorinated Styrene-Based Materials with Low Surface Energy Prepared by ATRP", Macromolecules, Jan. 2004, vol. 37, pp. 788-794.
Truelsen et al., "Synthesis by ATRP of triblock copolymers with densely grafted styrenic end blocks from a polyisobutylene macroinitiator", Marcomol. Rapid. Commun., Jul. 2, 1999, vol. 21, No. 2, pp. 1-5.
EESR for EP Application No. 15847536.8 dated Aug. 23, 2018, 6 pages.

\* cited by examiner

BLOCK COPOLYMER

CROSS-REFERENCE TO RELATED APPLICATIONS

The present application is a national phase entry under 35 U.S.C. § 371 of International Application No. PCT/KR2015/010334, filed Sep. 30, 2015, published in Korean, which claims priority to and the benefit of Korean Patent Application No. 2014-0131964, filed on Sep. 30, 2014, No. 2015-0079488, filed on Jun. 4, 2015, No. 2014-0175411, filed on Dec. 8, 2014, No. 2014-0175414, filed on Dec. 8, 2014, No. 2014-0175410, filed on Dec. 8, 2014, No. 2014-0175415, filed on Dec. 8, 2014, No. 2014-0175412, filed on Dec. 8, 2014, No. 2014-0175413, filed on Dec. 8, 2014, No. 2014-0175407, filed on Dec. 8, 2014, No. 2014-0175406, filed on Dec. 8, 2014, No. 2014-0175400, filed on Dec. 8, 2014, No. 2014-0175401, filed on Dec. 8, 2014, and No. 2014-0175402, filed on Dec. 8, 2014, the disclosures of which are incorporated herein by reference in their entirety.

FIELD

The present application relates to a block copolymer and its use.

BACKGROUND

A block copolymer has a molecular structure in which polymer blocks having different chemical structures are linked by covalent bonds. The block copolymer may form a periodically arranged structure such as a sphere, a cylinder or a lamella through phase separation. The size of a domain of the structure formed by self assembly of the block copolymer may be controlled in a wide range and it is possible various shapes of structures and therefore the block copolymer can be used, for example, in a pattern forming by a lithography, or magnetic recording media or various next generation nano device such as high density magnetic recording media, a nanowire line preparation, quantum dot or a metal dot.

DESCRIPTION

Oject

The present application provides a block copolymer, a polymer layer, a preparation method for a polymer layer and a pattern forming method, and the like.

Solution

An illustrative block copolymer may include a first block and a second block different from the first block. Each block of the block copolymer may be formed only using one type of monomer, or two or more types of monomers. The block copolymer may be a diblock copolymer only including one first block and one second block. Alternatively, the block copolymer may be a triblock copolymer including each one of the first block and the second block, and additionally any one or all of the first and second blocks, or additionally a third block, other than the first and second blocks.

Since the block copolymer includes two or more polymer chains linked by covalent bonds, phase separation occurs, and thereby a self-assembly structure is formed. The inventors confirmed that, when a block copolymer satisfies any one or two or more conditions that will be described below, a vertically-oriented self-assembly structure can also be formed on a surface of the trench substrate on which the above-described neutral treatment is not performed. Therefore, another aspect of the present application provides a block copolymer satisfying at least one of the conditions that will be described below. The shape or size of the nano-scale structure may be controlled by controlling the size, for example, a molecular weight, of a block copolymer, or relative ratios between blocks. The following conditions are parallel, and thus one condition is not prior to another condition. The block copolymer may satisfy any one, or two or more selected from the following conditions. It was shown that the block copolymer can have vertical orientation through satisfaction of any one of the following conditions. The term "vertical orientation" used herein refers to the orientation of the block copolymer, and may refer to orientation of the nano structure formed by the block copolymer, which is vertical to a substrate direction. For example, the vertical orientation may mean that an interface between a domain formed by the first block and a domain formed by the second block of the block copolymer is vertical to a surface of the substrate. The term "vertical" used herein is an expression allowing for an error, which includes, for example, an error within ±10, ±8, ±6, ±4 or ±2 degrees.

The technology controlling orientation of the structure in which the block copolymers are self-assembled on various types of substrates horizontally or vertically is a very big part of practical application of the block copolymer. Conventionally, the orientation of a nano structure on a film of the block copolymer is determined by which block is exposed to a surface or in the air. Generally, since a plurality of substrates are polar and the air is non-polar, among blocks of the block copolymer, a block having a higher polarity is wetted on a substrate, and a block having a lower polarity is wetted at an interface between the block and the air. Accordingly, to simultaneously wet blocks of the block copolymer, which have different characteristics, on a substrate, various techniques are suggested, and the most typical technique is control of orientation through manufacture of a neutral surface.

The inventor has confirmed that it becomes possible to realize the vertical orientation or vertical alignment even on the substrate to which any conventional treatment known for realizing the vertical orientation or alignment including the neutral brush layer is not performed by making the block copolymer to satisfy one, or two or more or all of the conditions as described below.

For example, a block copolymer according to one aspect of the present application may form the vertical orientation with respect to both of hydrophilic and hydrophobic surfaces on which special pretreatment is not performed.

Also, in another aspect of the present application, the vertical orientation described above may be induced within a short time in a large area through thermal annealing.

An illustrative block copolymer in the present application includes a first block and a second block having a different chemical structure from the first block, and the block copolymer is capable of forming a layer exhibiting an in-plane phase diffraction pattern of a Grazing Incidence Small-Angle X-ray Scattering on a surface of which a wetting angle of purified water is from 50 degrees to 70 degrees at room temperature and the block copolymer is capable of forming a layer exhibiting an in-plane phase diffraction pattern of a Grazing Incidence Small-Angle X-ray Scattering on a surface of which a wetting angle of purified water is from 5 degrees to 20 degrees at room temperature (Condition 1).

An illustrative block copolymer in the present application includes a first block and a second block having a different chemical structure from the first block, and the block copolymer or the first block may show a peak at an azimuth angle within −90 to −70 degrees, and a peak at an azimuth angle within 70 to 90 degrees of a diffraction pattern of a scattering vector in a range of 12 $nm^{-1}$ to 16 $nm^{-1}$ of the grazing incident wide angle X ray scattering (GIWAXS) spectrum (Condition 2).

An illustrative block copolymer used in the present application includes a first block and a second block having different chemical structure from the first block, and the block copolymer or the first block may show a melting transition peak or isotropic transition peak in a range of −80 to 200° C. through differential scanning calorimetry (DSC) analysis (Condition 3).

An illustrative block copolymer used in the present application includes a first block and a second block having a different chemical structure from the first block, and the block copolymer or the first block may show a peak having a full width at half maximum (FWHM) in a range of 0.2 to 0.9 $nm^{-1}$ within the range of a scattering vector (q) of 0.5 to 10 $nm^{-1}$ through XRD analysis (Condition 4).

An illustrative block copolymer used in the present application includes a first block and a second block having a different chemical structure from the first block. The first block includes a side chain, and the number (n) of chain-forming atoms of the side chain and the scattering vector (q) estimated by XRD analysis performed on the first block may satisfy the following Equation 2 (Condition 5).

$$3 \text{ nm}^{-1} \text{ to } 5 \text{ nm}^{-1} = nq/(2 \times \pi) \quad \text{[Equation 2]}$$

In Equation 2, n is the number of chain-forming atoms of the side chain, q is the smallest scattering vector (q) showing a peak in X-ray diffraction analysis performed on a block including the side chain, or a scattering vector (q) showing the peak having the largest peak area.

An illustrative block copolymer used in the present application includes a first block and a second block having a different chemical structure from the first block, and the absolute value of the difference in surface energy between the first block and the second block may be 10 mN/m or less (Condition 6).

An illustrative bock copolymer used in the present application includes a first block and a second block having a different chemical structure from the first block, and the absolute value of the difference in density between the first and second blocks may be 0.25 $g/cm^3$ or more (Condition 7).

An illustrative block copolymer used in the present application may include a first block and a second block having a different chemical structure from the first block, and the X determined by the below formula A may be 1.25 or more (Condition 8). Such a block copolymer may form a so called lamellar structure.

$$X = 1 + (D \times M)/(K \times L) \quad \text{[Formula A]}$$

In the Formula A, the D is a ratio (D2/D1) of a density (D2) of the second block relative to a density (D1) of the first block, the M is a ratio (M1/M2) of a molar mass (M1) of the first block relative to a molar mass (M2) of the second block, the K is a ratio (A2/A1) of a peak exhibited due to the second block in $^1$H-NMR relative to an area (A1) of a peak exhibited due to the first block in $^1$H-NMR and the L is a ratio (H1/H2) of a molar number (H1) of hydrogen atom in 1 mole of a repeating unit of the first block relative to a molar number (H2) of hydrogen atom in 1 mole of a repeating unit of the second block.

In the block copolymer, the first block may be a block including a side chain, which will be described below.

Hereinafter, the following conditions will be described in detail.

A. Condition 1

The block copolymer may form a layer exhibiting an in plane diffraction pattern of a Grazing Incidence Small-Angle X-ray Scattering (GISAXS) both on a hydrophilic surface and on a hydrophobic surface. The term "exhibiting an in plane diffraction pattern of a Grazing Incidence Small-Angle X-ray Scattering" may refer to a case where a peak perpendicular to an X coordinate is observed in a GISAXS analysis. Such a peak can be confirmed by vertical orientation of a block copolymer. Therefore, a block copolymer exhibiting the in plane diffraction pattern has a vertical orientation property. In an additional embodiment, at least two peaks may be confirmed at the X coordinate of the GISAXS diffraction pattern. In a case where a plurality of peaks are observed, the peaks with their scattering vector (the q value) having constant ratio can be observed. In the above case, the phase separation efficiency of the block copolymer can be further improved.

The block copolymer capable of forming a layer exhibiting the in plane diffraction pattern both on the hydrophilic surface and on the hydrophobic surface may have the vertical orientation property on various surfaces to which other treatment that has been performed for inducing the vertical orientation. The term "hydrophilic surface" as used herein may refer to a surface of which a wetting angle of purified water is from 5 degrees to 20 degrees. An example of the hydrophilic surface may include a surface of silicon treated with an oxygen plasma, sulfuric acid or piranha solution, but is not limited thereto. The term "hydrophobic surface" as used herein may refer to a surface of which a wetting angle of purified water is from 50 degrees to 70 degrees. An example of the hydrophobic surface may include a surface of PDMS (poly(dimethylsiloxane) treated with an oxygen plasma, a surface of silicon treated with HMDS (hexamethyldisilazane) or a surface of silicon treated with hydrogen fluoride (HF), but is not limited thereto.

In the present application, a physical property that can be changed by a temperature such as a wetting angle or density is, unless particularly defined otherwise, a value measured at a room temperature. The term "room temperature" is a natural temperature, which is not increased or decreased, for example, about 10 to 30° C., specifically, about 25 or 23° C.

The layer formed on the hydrophobic or hydrophilic surface and exhibiting the in plane phase diffraction pattern on GISAXS may be a layer which has been subjected to thermal annealing. The layer for the GISAXS analysis may be formed by a method including coating a coating solution, which is prepared by diluting the block copolymer in solvent (for example, fluorobenzene) so as to have a concentration of 0.7 weight %, on corresponding hydrophobic or hydrophilic surface so as to have a coating thickness of about 25 nm and a coating area of 2.25 $cm^2$ (width: 1.5 cm, length: 1.5 cm) and then subjecting the coated layer to thermal annealing. The thermal annealing may be performed by maintaining the layer at about 160° C. for an hour. The GISAXS may be performing by irradiating the layer with X ray having an incident angle from 0.12 to 0.23 degrees. The diffraction pattern scattered from the layer can be obtained by a conventional analysis device such as 2D marCCD. Methods for confirming the in plane diffraction pattern from the diffraction pattern are known in the field.

The block copolymer exhibiting the peak as described above in the GISAXS can show an excellent self assembling property and such property can be freely controlled according to an object.

B. Condition 2

One block of a block copolymer of the present application may show peaks at both of an azimuthal angle ranging from −90 to −70 degrees and an azimuthal angle ranging from 70 to 90 degrees of a diffraction pattern of a scattering vector in a range of 12 $nm^{-1}$ to 16 $nm^{-1}$ of a GIWAXS spectrum. The blocks showing the peaks may be blocks including side chains, which will be described below. In the specification, the block including the side chain may be a first block. Here, the azimuthal angle is an azimuthal angle when an angle of the diffraction pattern in an upper direction (direction of out-of-plane diffraction) is 0 degrees, which is measured in a clock-wise direction. In other words, the angle measured in the clock-wise direction is represented by a positive number, and the angle measured in a counter clock-wise direction is represented by a negative number. An FWHM observed at each azimuthal angle may be in a range of 5 to 70 degrees. The FWHM may be, in another embodiment, 7 degrees or more, 9 degrees or more, 11 degrees or more, 13 degrees or more, 15 degrees or more, 17 degrees or more, 19 degrees or more, 21 degrees or more, 25 degrees or more, 30 degrees or more, 35 degrees or more, 40 degrees or more, or 45 degrees or more. The FWHM may be, in another embodiment, 65 degrees or less or 60 degrees or less. A method of obtaining the GIWAXS spectrum is not particularly limited, and may be obtained by the following method of describing examples. A profile of a diffraction pattern peak of the obtained spectrum may be fitted through Gauss fitting, and therefrom, the FWHM may be obtained. In this case, when a half of the Gauss fitting result is obtained, the FWHM may be defined twice a value obtained from the result in which the half of the Gauss fitting result. In the Gauss fitting, a R square is in a range of about 0.26 to 0.95. That is, the above-described FWHM is observed at any one R square in the above range. A method of obtaining the above-described information is known in the art, and for example, a numerical analysis program such as Origin may be applied.

GIWAXS may be detected on a polymer prepared only using a monomer constituting a block to be detected. The block satisfying the condition 2 may be a block including an aromatic structure that does not include halogen atom or a block including the side chain. The block exhibiting the above peak at the above azimuthal angle in the GIWAXS may be aligned with having directional nature and can show an excellent phase separation or self assembling property or a vertical orientation property along with the other block.

C. Condition 3

The block copolymer of the present application or any one block of the block copolymer may show a melting transition peak or isotropic transition peak in a range of −80 to 200° C. through DSC analysis. When any one block of the block copolymer shows the above-described behavior in the DSC analysis, and the block copolymer including such a block simultaneously satisfies Conditions 2 and 3, the block showing the above behavior through the DSC analysis may be a block showing the peak in the GIWAXS described in Condition 2, that is, a peak showing at all of an azimuthal angle in a range of −90 to −70 degrees and an azimuthal angle in a range of 70 to 90 degrees of the diffraction pattern of a scattering vector in a range of 12 to 16 $nm^{-1}$ of the GIWAXS spectrum, for example, a first block. The block copolymer or any one block of the block copolymer may show any one or both of the melting transition peak and isotropic transition peak. Such a block copolymer may be a copolymer overall showing a crystal phase and/or liquid crystal phase, which are/is suitable for self-assembly, or showing such a crystal phase and/or liquid crystal phase.

The block copolymer showing the DSC behavior described above or any one block of the block copolymer may additionally satisfy the following condition in Condition 3.

For example, when the isotropic transition peak and the melting transition peak are simultaneously shown, the difference (Ti−Tm) between a temperature (Ti) at which the isotropic transition peak is shown and a temperature (Tm) at which the melting transition peak is shown may be in a range of 5 to 70° C. In another embodiment, the difference (Ti−Tm) may be 10° C. or more, 15° C. or more, 20° C. or more, 25° C. or more, 30° C. or more, 35° C. or more, 40° C. or more, 45° C. or more, 50° C. or more, 55° C. or more or 60° C. or more. The block copolymer or block copolymer including such a block having a difference (Ti−Tm) between the temperature (Ti) of the isotropic transition peak and the temperature (Tm) of the melting transition peak in the above range may have an excellent phase separation or self-assembly characteristic.

In another embodiment, when the isotropic transition peak and the melting transition peak are simultaneously shown, a ratio (M/I) of an area (I) of the isotropic transition peak and an area (M) of the melting transition peak may be in a range of 0.1 to 500. A block copolymer having the ratio (M/I) of the area (I) of the isotropic transition peak and the area (M) of the melting transition peak according to the DSC analysis or a block copolymer including such a block may maintain excellent phase separation or self-assembly characteristic. In another embodiment, the ratio (M/I) may be 0.5 or more, 1 or more, 1.5 or more, 2 or more, 2.5 or more, or 3 or more. Also, in another embodiment, the ratio (M/I) may be 450 or less, 400 or less, 350 or less, 300 or less, 250 or less, 200 or less, 150 or less, 100 or less, 90 or less, or 85 or less.

A method of performing the DSC analysis is known in the art, and in the present application, the analysis may be performed by such a known method.

A range of at temperature (Tm) at which the melting transition peak is shown may be in a range of −10° C. to 55° C. In another embodiment, the temperature (Tm) may be 50° C. or less, 45° C. or less, 40° C. or less, 35° C. or less, 30° C. or less, 25° C. or less, 20° C. or less, 15° C. or less, 10° C. or less, 5° C. or less, 0° C. or less.

The block copolymer may include a block having a side chain as will be described below. In this case, the block copolymer may satisfy the following Equation 1.

$$10° \text{ C.} \leq Tm - 12.25° \text{ C.} \times n + 149.5° \text{ C.} \leq 10° \text{ C.} \qquad \text{[Equation 1]}$$

In Equation 1, Tm may be the temperature at which the melting transition peak of the block copolymer or block having a side chain, and n is the number of chain-forming atoms of the side chain.

The block copolymer satisfying the above equation may have an excellent phase separation or self-assembly characteristic.

In Equation 1, Tm−12.25° C.×n+149.5° C. may be, in another embodiment, about −8 to 8° C., about −6 to 6° C. or about −5 to 5° C.

D. Condition 4

The block copolymer of the present application may include a block showing at least one peak within a predetermined range of scattering vectors (q) in X-ray Diffraction analysis (XRD analysis). When the block copolymer satisfies Condition 4 as well as Conditions 2 and/or 3, the block satisfying Conditions 2 and/or 3 may be a block satisfying Condition 4. The block satisfying Condition 4 may be the first block.

For example, any one block of the block copolymer may show at least one peak within the scattering vector (q) of 0.5 to 10 $nm^{-1}$ in the XRD analysis. The scattering vector (q) shown by the peak may be, in another embodiment, 0.7 $nm^{-1}$ or more, 0.9 $nm^{-1}$ or more, 1.1 $nm^{-1}$ or more, 1.3 $nm^{-1}$ or more, or 1.5 $nm^{-1}$ or more. The scattering vector (q) shown by the peak may be, in another embodiment, 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less, or 3 $nm^{-1}$ or less. An FWHM detected in the range of the scattering vector (q) may be in a range of 0.2 to 0.9 $nm^{-1}$. The FWHM may be, in another embodiment, 0.25, 0.3, 0.4 $nm^{-1}$ or more. The FWHM may be, in another embodiment, 0.85, 0.8, 0.75 $nm^{-1}$ or less.

In Condition 4, the term "full width at half maximum (FWHM)" may refer to a width (difference in scattering vector (q)) of a peak at a position showing ½ of the maximum peak intensity.

The scattering vector (q) and the FWHM in the XRD analysis is a value obtained by applying a numerical analysis method using a least square method on a result obtained by the following XRD analysis. In the above method, a part showing the least intensity in an XRD diffraction pattern may be set as a baseline to make the intensity 0, a profile of the XRD pattern peak is fitted by Gaussian fitting, and the scattering vector and the FWHM may be obtained from the fitted result. In the Gauss fitting, the R square is at least 0.9 or more, 0.92 or more, 0.94 or more or 0.96 or more. A method of obtaining such information from the XRD analysis is known in the art, and for example, a numerical analysis program such as Origin may be applied.

The block showing the FWHM in the range of the scattering vector (q) may include a crystal part suitable for self-assembly. The block copolymer including a block identified in the above-described range of the scattering vector (q) may have an excellent self-assembly characteristic.

The XRD analysis may be performed by measuring a scattering intensity according to a scattering vector after a sample was irradiated with x rays. The XRD analysis may be performed using a polymer prepared by polymerizing any one block of the block copolymer, for example, only a monomer constituting the first block. The XRD analysis may be performed on such a polymer without particular pretreatment, and for example, by irradiating the polymer with X rays after being dried under suitable conditions. As an X ray, an X ray having a vertical size of 0.023 mm and a horizontal size of 0.3 mm may be applied. An image of a 2D diffraction pattern may be obtained by scattering a sample using a measuring device (for example, 2D marCCD), and the obtained diffraction pattern may be fitted by the above-described method, thereby obtaining a scattering vector and an FWHM.

E. Condition 5

The block copolymer of the present application may include a block having a side chain, which will be described blow, as a first block, and the number (n) of chain-forming atoms of the side chain may satisfy the scattering vector (q) obtained by XRD analysis performed as shown in Condition 3 and the following Equation 2.

$$3 \text{ nm}^{-1} \text{ to } 5 \text{ nm}^{-1} = nq/(2\times\pi) \qquad \text{[Equation 2]}$$

In Equation 2, n is the number of chain-forming atoms, and q is the least scattering vector (q) showing a peak in the XRD analysis performed on the block including a side chain, or a scattering vector (q) showing a peak having the largest peak area. Also, in Equation 2, π is the circular constant.

The scattering vector introduced to Equation 2 is a value obtained by the same method described in the XRD analysis method.

The scattering vector (q) introduced to Equation 2 may be, for example, in a range of 0.5 to 10 $nm^{-1}$. The scattering vector (q) introduced to Equation 2 may be, in another embodiment, 0.7 $nm^{-1}$ or more, 0.9 $nm^{-1}$ or more, 1.1 $nm^{-1}$ or more, 1.3 $nm^{-1}$ or more, 1.5 $nm^{-1}$ or more. The scattering vector (q) introduced to Equation 2 may be, in another embodiment, 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less, 3 $nm^{-1}$ or less.

Equation 2 shows the relation between the distance (D) between polymer main chain including the side chain and the number of chain-forming atoms when a film is formed of a polymer constituting only a block having the side chain of the block copolymer, and when the number of chain-forming atoms of the side chain of the polymer having the side chain satisfies Equation 2, crystallinity of the side chain is increased, and thus a phase separation characteristic or vertical orientation of the block copolymer may be highly enhanced. The nq/(2×π) according to Equation 2 may be, in another embodiment, 4.5 $nm^{-1}$ or less. Here, the distance between main chains of the polymer having the side chain (D, unit: nm) may be calculated by Equation D=2×π/q, in which D is the distance (D, unit: nm), and π and q are defined in Equation 2.

F. Condition 6

The absolute value of the difference in surface energy between the first block and the second block of the block copolymer of the present application may be 10, 9, 8, 7.5, 7 mN/m or less. The absolute value of the difference in surface energy may be 1.5, 2, 2.5 mN/m or more. A structure in which the first block and the second block having the above range of the absolute value of the difference in surface energy are linked by covalent bonds may direct effective microphase separation by phase separation caused by suitable non-compatibility. Here, the first block may be, for example, a block having a side chain which will be described above, or a block having an aromatic structure without a halogen atom.

The surface energy may be measured using a drop-shape analyzer (DSA100, KRUSS). Particularly, the surface energy may be measured on a film prepared by applying a coating solution prepared by diluting a target sample (a block copolymer or a homopolymer) for measuring surface energy with fluorobenzene at a concentration of a solid content of about 2 wt % onto a substrate to have a thickness of about 50 nm and a coating area of 4 $cm^2$ (width: 2 cm, length: 2 cm), drying the substrate at room temperature for about 1 hour, and thermal-annealing the dried substrate at 160° C. for about 1 hour. A process of measuring a contact angle by dropping deionized water whose surface tension is known onto the thermal-annealed film is repeated five times, thereby obtaining a mean value of the obtained five contact angles, and a process of obtaining a contact angle by dropping diiodomethane whose surface tension is known in the same manner as describe above is repeated five times, thereby obtaining a mean value of the obtained five contact angles. Afterward, surface energy may be obtained by substituting a value for surface tension (Strom value) of a solvent by the Owens-Wendt-Rabel-Kaelble method using a mean value of the obtained contact angles for the deionized water and diiodomethane, thereby obtaining surface energy. A value of the surface energy for each block of the block copolymer may be calculated on a homopolymer prepared only using a monomer forming the block.

When the block copolymer includes the above-described side chain, the block having the side chain may have higher surface energy than other blocks. For example, when the first block of the block copolymer includes a side chain, the first block may have higher surface energy than the second block. In this case, the surface energy of the first block may be in a range of about 20 to 40 mN/m. The surface energy of the first block may be 22, 24, 26, 28 mN/m or more. The surface energy of the first block may be 38, 36, 34, 32 mN/m or less. The block copolymer including the first block and having the different in surface energy as described above from the second block may have an excellent self-assembly characteristic.

G. Condition 7

The absolute value of a difference in density between the first block and the second block in the block copolymer may be 0.25 g/cm$^3$ or more, 0.3 g/cm$^3$ or more, 0.35 g/cm$^3$ or more, 0.4 g/cm$^3$ or more, or 0.45 g/cm$^3$ or more. The absolute value of the difference in density may be 0.9 g/cm$^3$ or less, 0.8 g/cm$^3$ or less, 0.7 g/cm$^3$ or less, 0.65 g/cm$^3$ or less, or 0.6 g/cm$^3$ or less. A structure in which the first block and the second block having the above range of the absolute value of the difference in density are linked by covalent bonds may direct effective microphase separation by phase separation caused by suitable non-compatibility.

The density of each block of the block copolymer may be measured using a known buoyancy method, and for example, the density may be measured by analyzing the mass of the block copolymer in a solvent having known mass and density in the air, such as ethanol.

When the above-described side chain is included, the block having the side chain may have a lower density than other blocks. For example, when the first block of the block copolymer includes the side chain, the first block may have a lower density than the second block. In this case, the density of the first block may be in a range of about 0.9 to 1.5 g/cm$^3$. The density of the first block may be 0.95 g/cm$^3$ or more. The density of the first block may be 1.4 g/cm$^3$ or less, 1.3 g/cm$^3$ or less, 1.2 g/cm$^3$ or less, 1.1 g/cm$^3$ or less, or 1.05 g/cm$^3$ or less. The block copolymer including the first block and having the difference in density from the second block may have an excellent self-assembly characteristic.

H. Condition 8

A block copolymer of the present application may have the X value determined by the formula A of 1.25 or more. The block copolymer having the X value determined by the formula A of 1.25 may be a diblock copolymer including only the first and the second blocks.

$$X=1+(D\times M)/(K\times L) \quad \text{[Formula A]}$$

In the Formula A, the D is a ratio (D2/D1) of a density (D2) of the second block relative to a density (D1) of the first block, the M is a ratio (M1/M2) of a molar mass (M1) of the first block relative to a molar mass (M2) of the second block, the K is a ratio (A2/A1) of an area (A2) of a peak exhibited due to the second block in $^1$H-NMR relative to an area (A1) of a peak exhibited due to the first block in $^1$H-NMR and the L is a ratio (H1/H2) of a molar number (H1) of hydrogen atom in 1 mole of a repeating unit of the first block relative to a molar number (H2) of hydrogen atom in 1 mole of a repeating unit of the second block.

The method for detecting 1H-NMR for obtaining the K value in the formula A is not particularly limited and may be performed according to a conventional process. An illustrative detecting method will be described in the below Example. The method calculating an area of a peak from the result of NMR analysis is known in the field. For example, in a case where a peak due to the first block is not overlapped with a peak due to the second block, it can be obtained from an area of a corresponding peak and, in a case where they are overlapped, the ratio can be obtained by considering the overlapped region. Various analysis program capable of obtaining the area of the peak by translating $^1$H-NMR spectrum are known in the field and, for example, the area of the peak can be calculated by using MestReC program.

The density of each block of the block copolymer, which is used for obtaining the D value in the formula A, may be measured using a known buoyancy method, and for example, the density may be measured by analyzing the mass of the block copolymer in a solvent having known mass and density in the air, such as ethanol. The density of each block may be obtained, for example, with respect to a homopolymer prepared only by monomers forming a corresponding block by the buoyancy method.

The M value applied in the formula A is a ratio of molar masses of repeating units of blocks of the block copolymer as described above. The molar mass can be obtained by a conventional method. For example, the M value may be obtained by using a ratio of molar mass of each monomer forming each block of the block copolymer. In a case where the block includes at least two kinds of monomers, the molar mass for calculating the M value may be molar mass of a monomer included in the largest molar number in the block.

The L value in the formula A is a ratio of numbers of hydrogen atom in 1 mole of a repeating unit of the block in the block copolymer. The ratio may be obtained based on a chemical structure of each repeating unit. For example, it can be obtained from a number of hydrogen atom in the chemical structure of a monomer forming each block in the block copolymer or from the result of $^1$H NMR. In a case where the block includes at least two kinds of monomers, the number for calculating the L value may be molar mass of a monomer included in the largest molar number in the block.

The X in the formula A is a value representing a ratio of the first and the second blocks in the block copolymer. Conventionally, the ratio of blocks in the block copolymer was confirmed based on molecular weights obtained from GPC and the like; however it has been confirmed that the above conventional method cannot reflect actual ratio between blocks and therefore it cannot be possible to obtain a block copolymer as designed. For example, in a case where a block copolymer is synthesized by using one block of the block copolymer as a macroinitiator as described below, according to a reactivity of the macroinitiator and monomers, there is a case where a block copolymer including each block as designed is not synthesized; however the above cannot be accurately confirmed by the GPC.

In one embodiment, the X according to the formula A may be about 1.3 or more, about 1.35 or more, about 1.4 or more, about 1.45 or more, about 1.5 or more, about 1.6 or more or about 1.65 or more. In another embodiment, the X according to the formula A may be about 10 or less, about 9.5 or less, about 9 or less, about 8.5 or less, about 7.5 or less or about 7 or less.

In another embodiment, the X according to the formula A may be from about 2.5 to 6.7, from about 2.5 to 5 or from about 2.8 to 5. Such a block copolymer may form a so called cylinder structure or a self assembled structure in which the cylinder has superiority. In another embodiment, the X according to the formula A may be from about 1.65 to 2.5, from about 1.8 to 2.5 or from about 1.8 to 2.3. Such a block copolymer may form a so called lamellar structure or a self assembled structure in which the lamellar has superiority.

For example, in a case where the first block is a block including an aromatic structure that does not has halogen atom included along with the second block that is a block including an aromatic structure substituted with halogen atom or the first block is a block including a side chain included along with the second block that is a block including halogen atom, the block copolymer having the above X value is capable of forming a vertically oriented structure effectively.

As described above, the block copolymer may satisfy any one or two or more selected from Conditions 1 to 8.

For example, the block copolymer may be a block copolymer satisfying Condition 1, 2, 3, 4, 5, 6, 7 or 8.

As another condition, a number average molecular weight (Mn) of the block copolymer may be, for example, in a range of 3,000 to 300,000. The term "number average molecular weight" is a conversion value with respect to standard polystyrene measured by gel permeation chromatography (GPC), and the term "molecular weight" used herein means, unless particularly defined otherwise, the number average molecular weight (Mn). The molecular weight (Mn) may be, in another embodiment, for example, 3000 or more, 5000 or more, 7000 or more, 9000 or more, 11000 or more, 13000 or more, or 15000 or more. The molecular weight (Mn) may be, in still another embodiment, about 250000 or less, 200000 or less, 180000 or less, 160000 or less, 140000 or less, 120000 or less, 100000 or less, 90000 or less, 80000 or less, 70000 or less, 60000 or less, 50000 or less, 40000 or less, 30000 or less, or 25000 or less. The block copolymer may have a polydispersity (Mw/Mn) in a range of 1.01 to 1.60. The polydispersity may be, in another embodiment, about 1.1 or more, 1.2 or more, 1.3 or more, or 1.4 or more.

In such a range, the block copolymer may have a suitable self-assembly characteristic. The number average molecular weight of the block copolymer may be controlled by considering a desired self-assembly structure.

The above-described conditions may be satisfied by, for example, control of the structure of the block copolymer. For example, at least one or all of the first and second blocks in the block copolymer satisfying one or more of the above-described conditions may at least include an aromatic structure. All of the first block and the second block may include an aromatic structure, and in this case, the aromatic structure included in the first and second blocks may be the same as or different from each other. Also, at least one of the first and second blocks of the block copolymer satisfying one or more of the above-described conditions may include the above-described side chain, or at least one halogen atom, which will be described below, and the side chain and the halogen atom may be substituted by the aromatic structure. The block copolymer of the present application may include two or more blocks.

As described above, the first and/or second block(s) of the block copolymer may include an aromatic structure. Such an aromatic structure may be included in only one or both of the first and second blocks. When both of the blocks include aromatic structures, the aromatic structures of the blocks may be the same as or different from each other.

The term "aromatic structure" used herein refers to the structure of an aromatic compound, and the term "aryl group" may refer to a monovalent residue derived from the aromatic compound, and "arylene group" may refer to a bivalent residue derived from the aromatic compound. Here, the aromatic compound is, unless particularly defined otherwise, a compound which has a benzene ring, or two or more benzene rings, which are linked by sharing one or two carbon atoms or with an optional linker, or a derivative thereof. Therefore, the aryl group, that is, the monovalent residue derived from the aromatic compound may refer to a substituent in which a radical formed by releasing one hydrogen atom of the aromatic compound forms a covalent bond, and the arylene group, that is, the bivalent residue derived from the aromatic compound may refer to a substituent in which a radical formed by releasing two hydrogen atoms of the aromatic compound forms a covalent bond. The aryl group or arylene group may be, for example, an aryl group or arylene group having 6 to 30, 6 to 25, 6 to 21, 6 to 18, or 6 to 13 carbon atoms. As the aryl group or arylene group, a monovalent or bivalent residue derived from benzene, naphthalene, azobenzene, anthracene, phenanthrene, tetracene, pyrene or benzopyrene may also be used. The term "aromatic structure" used herein may used as the same meaning as the aryl group or arylene group.

The aromatic structure may be a structure included in the block main chain or a structure linked to the block main chain as a side chain. The above-described conditions can be adjusted by suitable control of the aromatic structure which can be included in each block.

In one embodiment, the block copolymer satisfying at least one of the conditions may include a first block including a side chain and a second block different from the first block. Here, the side chain may be a side chain having 8 or more chain-forming atoms, which will be described below. The first block may be a block satisfying any one, two or more, or all of Conditions 2, 3, 4 and 5.

The first block may include a ring structure, and the side chain may be substituted in the ring structure. The ring structure may be the above-described aromatic structure, an aryl or arylene group, or an alicyclic ring structure. Such a ring structure may be a ring structure without having a halogen atom.

The "alicyclic ring structure" used herein refers to, unless particularly defined otherwise, a cyclic hydrocarbon structure, not an aromatic ring structure. The alicyclic ring structure may be included in the block copolymer in the form of a monovalent or bivalent residue. The alicyclic ring structure may be, unless particularly defined otherwise, for example, an alicyclic ring structure having 3 to 30, 3 to 25, 3 to 21, 3 to 18, or 3 to 13 carbon atoms.

The second block included along with the first block is a block, which is chemically different from the first block. The second block may be, for example, a block including a halogen atom, for example, a chlorine atom or fluorine atom. The second block may include 1 or more, 2 or more, 3 or more, 4 or more, or 5 or more halogen atoms. The number of halogen atoms may be, for example, 30 or less, 25 or less, 20 or less, 15 or less, 10 or less, 9 or less, 8 or less, 7 or less, 6 or less, or 5 or less. The second block may include a ring structure, and the halogen atom may be substituted in such a ring structure. The ring structure may be the above-described aromatic structure, aryl or arylene group.

The term "side chain" used herein means a chain linked to the main chain of a polymer, and the term "chain-forming atom" means an atom forming a linear structure of the chain as an atom forming the side chain. The side chain may be linear or branched, but the number of chain-forming atoms may be calculated only as the number of atoms constituting the longest linear chain, not including another atom binding to the chain-forming atom (for example, when the chain-forming atom is a carbon atom, a hydrogen atom binding to the carbon atom). For example, in the case of a branched chain, the number of chain-forming atoms may be calculated as the number of chain-forming atoms constituting the longest chain. For example, when the side chain is n-pentyl group, all of the chain-forming atoms are carbons, the number of which is 5, and even when the side chain is 2-methylpentyl group, all of the chain-forming atoms are carbon, the number of which is 5. As the chain-forming atom, carbon, oxygen, sulfur or nitrogen may be used, and a suitable chain-forming atom may be carbon, oxygen or nitrogen, or carbon or oxygen. The number of chain-forming atoms may be 8 or more, 9 or more, 10 or more, 11 or more, or 12 or more. The number of chain-forming atoms may also, 30 or less, 25 or less, 20 or less, or 16 or less.

To control the above-described condition, a chain having 8 or more chain-forming atoms may be linked to a side chain of the first block of the block copolymer. The terms "chain" and "side chain" used herein may refer to the same subjects.

The side chain may be, as described above, a chain having 8 or more, 9 or more, 10 or more, 11 or more, or 12 or more chain-forming atoms. The number of chain-forming atoms may also be 30 or less, 25 or less, 20 or less, or 16 or less. The chain-forming atom may be a carbon, oxygen, nitrogen or sulfur atom, and preferably, carbon or oxygen.

As a side chain, a hydrocarbon chain such as an alkyl group, an alkenyl group or an alkynyl group may be used. At least one of the carbon atoms of the hydrocarbon chain may be substituted with a sulfur atom, an oxygen atom or a nitrogen atom.

When the side chain is linked to a ring structure such as an aromatic structure, the chain may be directly linked to the ring structure, or linked by means of a linker. As the linker, an oxygen atom, a sulfur atom, —$NR_1$—, —$S(=O)_2$—, a carbonyl group, an alkylene group, an alkenylene group, an alkynylene group, —C(=O)—$X_1$— or —$X_1$—C(=O)— may be used. Here, $R_1$ is a hydrogen, an alkyl group, an alkenyl group, an alkynyl group, an alkoxy group or an aryl group, $X_1$ is a single bond, an oxygen atom, a sulfur atom, —$NR_2$—, —$S(=O)_2$—, an alkylene group, an alkenylene group or an alkynylene group, and here, $R_2$ may be a hydrogen, an alkyl group, an alkenyl group, an alkynyl group, an alkoxy group or an aryl group. As a suitable linker, an oxygen atom may be used. The side chain may be linked to a ring structure such as an aromatic structure, for example, by means of an oxygen atom or nitrogen atom.

When the above-described ring structure such as an aromatic structure is linked to the main chain of the block as a side chain, the aromatic structure may also be directly linked or may be linked to the main chain by means of a linker. In this case, as a linker, an oxygen atom, a sulfur atom, —$S(=O)_2$—, a carbonyl group, an alkylene group, an alkenylene group, an alkynylene group, —C(=O)—$X_1$— or —$X_1$—C(=O)— may be used, and in this case, $X_1$ is a single bond, an oxygen atom, a sulfur atom, —$S(=O)_2$—, an alkylene group, an alkenylene group or an alkynylene group. As a suitable linker linking the aromatic structure to the main chain, —C(=O)—O— or —O—C(=O)— may be used, but the present application is not limited thereto.

In another embodiment, the aromatic structure included in the first and/or second block(s) of the block copolymer may include 1 or more, 2 or more, 3 or more, 4 or more, or 5 or more halogen atoms. The number of halogen atoms may be, for example, 30 or less, 25 or less, 20 or less, 15 or less, or 10 or less. As the halogen atom, fluorine or chlorine may be used, and the fluorine atom is preferably used. As described above, the block having the aromatic structure including the halogen atom may efficiently implement a phase-separated structure through a suitable interaction with other blocks.

As the aromatic structure including a halogen atom, an aromatic structure having 6 to 30, 6 to 25, 6 to 21, 6 to 18, or 6 to 13 carbon atoms may be used, but the present application is not limited thereto.

In the block copolymer, all of the first and second blocks include aromatic structures, in order to implement a suitable phase-separated structure, the first block may include an aromatic structure without including a halogen atom, and the second block may include an aromatic structure including a halogen atom. Also, the above-described side chain may be directly linked or linked by means of a linker including oxygen or nitrogen to the aromatic structure of the first block.

When the block copolymer includes a block having a side chain, the block may be, for example, a block including the unit represented by Formula 1. The block may be a block including the following unit of Formula 1 as a main component. The expression "a block includes a unit as a main component" used herein may mean that the block includes the unit at 60% or more, 70% or more, 80% or more, 90% or more, or 95% or more based on a weight, or 60 mol % or more, 70 mol % or more, 80 mol % or more, 90 mol % or more, or 95 mol % or more.

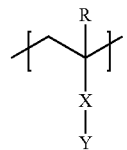

[Formula 1]

In Formula 1, R is a hydrogen or an alkyl group, X is a single bond, an oxygen atom, a sulfur atom, —$S(=O)_2$—, a carbonyl group, an alkylene group, an alkenylene group, an alkynylene group, —C(=O)—$X_1$— or —$X_1$—C(=O)—, and in this case, $X_1$ is an oxygen atom, a sulfur atom, —$S(=O)_2$—, an alkylene group, an alkenylene group or an alkynylene group, and Y is a monovalent substituent including a ring structure to which the side chain having a chain-forming atom is linked.

The term "single bond" used herein may refer to the case in which a separate atom is not present in the corresponding part. For example, when the X in Formula 1 is a single bond, a structure in which the Y is directly bound to a polymer chain may be formed.

The term "alkyl group" used herein may refer to, unless particularly defined otherwise, an alkyl group having 1 to 20, 1 to 16, 1 to 12, 1 to 8, or 1 to 4 carbon atoms. The alkyl group may be a linear, branched or cyclic alkyl group, and may be optionally substituted with one or more one substituent. However, in a case where the side chain is an alkyl group, the alkyl group may has 8 or more, 9 or more, 10 or more, 11 or more, or 12 or more carbon atoms and the number of the carbon atoms may be 30 or less, 25 or less, 20 or less or 16 or less.

The term "alkenyl group" or "alkynyl group" used herein may refer to, unless particularly defined otherwise, an alkenyl group or alkynyl group having 2 to 20, 2 to 16, 2 to 12, 2 to 8, or 2 to 4 carbon atoms. The alkenyl group or alkynyl group may be a linear, branched or cyclic alkenyl or alkynyl group, and may be optionally substituted with one or more substituent. However, in a case where the side chain is an alkenyl or alkynyl group, the alkenyl or alkynyl group may has 8 or more, 9 or more, 10 or more, 11 or more, or 12 or more carbon atoms and the number of the carbon atoms may be 30 or less, 25 or less, 20 or less or 16 or less.

The term "alkylene group" used herein may be, unless particularly defined otherwise, an alkylene group having 1 to 20, 1 to 16, 1 to 12, 1 to 8, or 1 to 4 carbon atoms. The alkylene group may be a linear, branched or cyclic alkylene group, and may be optionally substituted with one or more substituent.

The term "alkenylene group or alkynylene group" used herein may refer to, unless particularly defined otherwise, an alkenylene or alkynylene group having 2 to 20, 2 to 16, 2 to 12, 2 to 8, or 2 to 4 carbon atoms. The alkenylene group or alkynylene group may be a linear, branched or cyclic alkenylene or alkynylene group, and may be optionally substituted with one or more substituent.

In one embodiment, the X in the Formula 1 may be —C(=O)O— or —OC(=O)—.

The Y in the formula 1 is the substituent including the chain, it may be a substituent including, for example, an aromatic structure having 6 to 18 or 6 to 12 carbon atoms. In the above, the chain may be an alkyl group having 8 or more, 9 or more, 10 or more, 11 or more or 12 or more carbon atoms. The alkyl group may include 30 or less, 25 or less, 20 or less or 16 or less carbon atom. The chain may be directly linked to the aromatic structure or be linked to the aromatic structure via the linker as described above.

The first block may be, in another embodiment, a unit represented by the Formula 2 below.

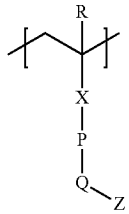

[Formula 2]

In Formula 2, the R may be the hydrogen atom or the alkyl group having 1 to 4 carbon atom(s), the X may be —C(=O)—O—, the P may be the arylene group having 6 to 12 carbon atoms, the Q may be the oxygen atom, the Z is the chain having 8 or more chain-forming atoms.

In another embodiment of the Formula 2, the P may be a phenylene. Also, the Z may be a linear alkyl group having 9 to 20, 9 to 18 or 9 to 16. In a case where the P is the phenylene, the Q may be linked to the para position of the phenylene. The alkyl group, arylene group, phenylene group and the chain may be optionally substituted with at least one substituent.

In a case where the block copolymer includes the block comprising the aromatic structure comprising the halogen atom, for example as the second block, the block may be a block represented by Formula 3 below. The block may include the unit of Formula 3 as a main component.

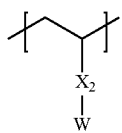

[Formula 3]

In Formula 3, the $X_2$ may be a single bond, an oxygen atom, a sulfur atom, —S(=O)$_2$—, an alkylene group, an alkenylene group, an alkynylene group, —C(=O)—$X_1$— or —$X_1$—C(=O)—, where the $X_1$ is a single bond, an oxygen atom, a sulfur atom, —S(=O)$_2$—, an alkylene group, an alkenylene group or an alkynylene group, and the W may be an aryl group including at least one halogen atom.

In another embodiment of the Formula 3, the $X_2$ may be the single bond or the alkylene group.

In the Formula 3, the aryl group of the W may be an aryl group having 6 to 12 carob atoms or a phenyl group. The aryl group or the phenyl group may include 1 or more, 2 or more, 3 or more, 4 or more or 5 or more halogen atom(s). The number of the halogen atom(s) may be 30 or less, 25 or less, 20 or less, 15 or less or 10 or less. As the halogen atom, fluorine atom may be used.

The block of the Formula 3 may be, in another embodiment, represented by Formula 4 below.

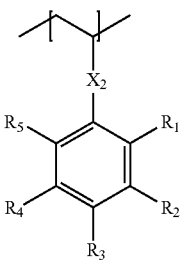

[Formula 4]

In Formula 4, the $X_2$ is the same as defined in the Formula 3, and the $R_1$ to $R_5$ may be each independently hydrogen, an alkyl group, a haloalkyl group or a halogen atom. The number of the halogen atom included in the $R_1$ to $R_5$ is 1 or more.

In Formula 4, the $R_1$ to $R_5$ may be each independently hydrogen, an alkyl group having 1 to 4 carbon atom(s) or a haloalkyl group having 1 to 4 carbon atom(s) or the halogen atom, and the halogen atom may be the fluorine or chlorine.

In Formula 4, the $R_1$ to $R_5$ may include 1 or more, 2 or more, 3 or more, 4 or more, 5 or more or 6 or more halogen atom(s). The upper limit of the number of the halogen atom(s) is not particularly limited, and the number of the halogen atom(s) in the $R_1$ to $R_5$ may be, for example, 12 or less, 8 or less, or 7 or less.

The block copolymer may include only the above described two kinds of blocks or may include one or both of the above described two kinds of blocks along with another block.

In one embodiment, one block among two blocks, for example the first and the second blocks of the block copolymer may be a crosslinkable block. By making one block to be crosslinkable, an etching selectivity can be improved. In order to make the block to be crosslinkable, a crosslinkable substituent may be incorporated into the block. As the crosslinkable substituent that may be incorporated into the block, a functional group that can be crosslinked by ultraviolet ray or heat such as a functional group including unsaturated double bond or a functional group including sulfur, a functional group including azide such as azidealkylcarbonyl oxy group, glycidyl azide or hydroxyphenyl azide, benzoylphenoxy group, alkenyloxycarbonyl, (meth)acryloyl group or alkenyloxyalkyl group may be illustrated, but is not limited thereto.

The crosslinkable group may be incorporated into the unit of the block as described above or into the block as a separated unit.

A specific method of preparing the above-described block copolymer is not particularly limited. For example, the block copolymer may be prepared by a living radical polymerization (LRP) method using the monomer. For example, anionic polymerization for synthesizing a block copolymer using an organic rare earth metal complex as a polymerization initiator or using an organic alkali metal compound as a polymerization initiator in the presence of an inorganic acid salt such as a salt of an alkali metal or alkali earth metal, atom transfer radical polymerization (ATRP) using an atom transfer radical polymerizer as a polymerization control agent, activators regenerated by electron transfer (ARGET) atom transfer radical polymerization (ATRP) performing polymerization using an atom transfer radical polymerizer as a polymerization control agent in the presence of an organic or inorganic reducing agent generating electrons, initiators for continuous activator regeneration (ICAR) atom transfer radical polymerization (ATRP), reversible addition-fragmentation chain transfer (RAFT) using an inorganic reducing agent RAFT agent, or a method using an organic tellurium compound as an initiator may be used, and a suitable one may be selected from the above-described methods.

For example, the block copolymer may be prepared by a method including polymerizing a reactant including monomers capable of forming the block through living radical polymerization in the presence of a radical initiator and a living radical polymerization reagent. The process of preparing a block copolymer may further include, for example, precipitating a polymerization product produced through the above-described process in a non-solvent.

The type of a radical initiator is not particularly limited, and therefore a radical initiator may be suitably selected by considering polymerization efficiency. For example, as a radical initiator, an azo compound such as azobisisobutyronitrile (AIBN) or 2,2'-azobis-(2,4-dimethylvaleronitrile), or a peroxide such as benzoyl peroxide (BPO) or di-t-butyl peroxide (DTBP) may be used.

The living radical polymerization may be performed in a solvent such as methylene chloride, 1,2-dichloroethane, chlorobenzene, dichlorobenzene, benzene, toluene, acetone, chloroform, tetrahydrofuran, dioxane, monoglyme, diglyme, dimethylformamide, dimethylsulfoxide or dimethylacetamide.

As a non-solvent, for example, an alcohol such as methanol, ethanol, normal propanol or isopropanol, a glycol such as ethyleneglycol, or an ether such as n-hexane, cyclohexane, n-heptane or petroleum ether may be used, but the present application is not limited thereto.

The present application relates to a polymer layer including the block copolymer. The polymer layer may be used in various applications. For example, it can be used in a biosensor, a recording media such as a flash memory, a magnetic storage media or the pattern forming method or an electric device or an electronic device, and the like.

In one embodiment, the block copolymer in the polymer layer may be forming a periodic structure including a sphere, a cylinder, a gyroid, or a lamella by the self assembly. For example, in one segment of the first block or the second block or other block linked to the above block via a covalent bond in the block copolymer, other segment may be forming the regular structure such as lamella form, cylinder form and the like. And the above structure may be aligned vertically.

The polymer layer may show the above in-plane phase diffraction pattern, i.e., the peak vertical to the X coordinate in the GISAXS diffraction pattern of the GISAXS analysis. In further embodiment, two or more peaks may be observed in the X coordinate of the GISAXS diffraction pattern. In a case where two or more peaks are observed, the scattering vectors (the q values) may be confirmed with having constant ratios.

The present application relates also to a method for forming a polymer layer by using the block copolymer. The method may include forming a polymer layer including the block copolymer on a substrate in a self-assembled state. For example, the method may include forming a layer by coating the block copolymer or a coating solution including the block copolymer and then aging it. The aging may be a thermal annealing or a solvent annealing.

The thermal annealing may be performed based on, for example, a phase transition temperature or glass transition temperature of the block copolymer, and for example, may be performed at a temperature higher than the glass transition temperature or phase transition temperature. A time for the heat treatment is not particularly limited, and the heat treatment may be performed for approximately 1 minute to 72 hours, but may be changed if necessary. In addition, the temperature of the heat treatment of the polymer layer may be, for example, 100° C. to 250° C., but may be changed in consideration of the block copolymer used herein.

The solvent annealing may be performed in a non-polar solvent and/or a polar solvent at the room temperature for approximately 1 minute to 72 hours.

The present application relates also to a pattern-forming method. The method may include selectively removing the first or second block of the block copolymer from a laminate comprising a substrate and a polymer layer that is formed on a surface of the substrate and that includes a self-assembled block copolymer. The method may be a method for forming a pattern on the above substrate. For example, the method may include forming the polymer layer on the substrate, selectively removing one block or two or more blocks of the block copolymer that is in the polymer layer; and then etching the substrate. By the above method, for example, nano-scaled micropattern may be formed. Further, according to shapes of the block copolymer in the polymer layer, various shapes of pattern such as nano-rod or nano-hole can be formed by the above method. If necessary, in order to form a pattern, the block copolymer may be mixed with another copolymer or homopolymer. A kind of the substrate applied to this method may be selected without particular limitation, and, for example, silicon oxide and the like may be applied.

For example, according to the method, a nano-scale pattern of silicon oxide having a high aspect ratio may be formed. For example, various types of patterns such as a nanorod or nanohole pattern may be formed by forming the polymer layer on the silicon oxide, selectively removing any one block of the block copolymer in a state where the block copolymer in the polymer layer is formed in a predetermined structure, and etching the silicon oxide in various methods, for example, reactive ion etching. In addition, according to the above method, a nano pattern having a high aspect ratio can be formed.

For example, the pattern may be formed to a scale of several tens of nanometers, and such a pattern may be applied in various uses including a next-generation information electronic magnetic recording medium.

For example, a pattern in which nano structures, for example, nanowires, having a width of approximately 10 to 40 nm are disposed at an interval of approximately 20 to 80 nm may be formed by the above-described method. In another embodiment, a structure in which nanoholes having a width, for example, a diameter of approximately 3 to 40 nm are disposed at an interval of approximately 6 to 80 nm can be implemented.

In addition, in this structure, nanowires or nanoholes may be formed to have a high aspect ratio.

In this method, a method of selectively removing any one block of the block copolymer is not particularly limited, and for example, a method of removing a relatively soft block by irradiating a suitable electromagnetic wave, for example, ultra violet rays to a polymer layer may be used. In this case, conditions for ultra violet radiation may be determined according to a type of the block of the block copolymer, and ultra violet rays having a wavelength of approximately 254 nm may be irradiated for 1 to 60 minutes.

In addition, followed by the ultra violet radiation, the polymer layer may be treated with an acid to further remove a segment degraded by the ultra violet rays.

In addition, the etching of the substrate using the polymer layer from which a block is selectively removed may be performed by reactive ion etching using CF4/Ar ions, and followed by the above process, and removing the polymer layer from the substrate by oxygen plasma treatment may be further performed.

EFFECT

Figure 1:
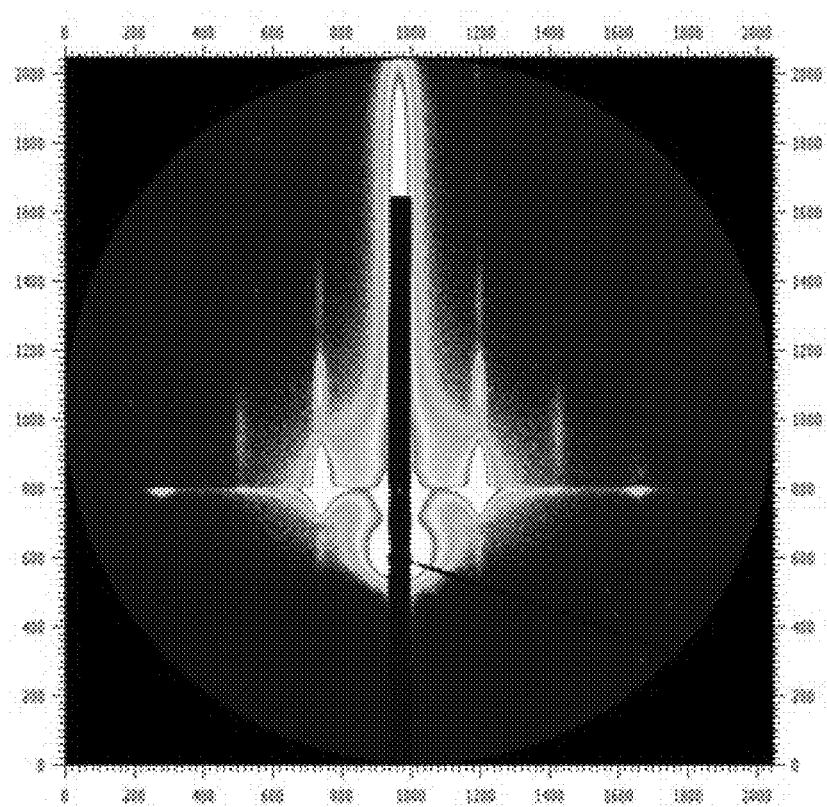
FIGS. 1 and 2 are drawings of GISAXS diffraction patterns.

The present application can provides a block copolymer that has an excellent self assembling property or phase separation property and therefore can be used in various applications and its use.

DETAILED DESCRIPTION OF EMBODIMENTS

Hereinafter, the present application will be described in further detail with reference to examples according to the present application, but the scope of the present application is not limited to the following examples.

1. NMR Analysis

NMR analysis was performed at room temperature using an NMR spectrometer including a Varian Unity Inova (500 MHz) spectrometer having a triple resonance 5 mm probe. A subject for analysis was diluted with a solvent ($CDCl_3$) for measuring NMR at a concentration of about 10 mg/ml, and chemical shift was expressed in ppm.

Abbreviations br=broad signal, s=singlet, d=doublet, dd=doublet of doublets, t=triplet, dt=doublet of triblets, q=quartet, p=quintet, m=multiplet.

2. Gel Permeation Chromatography (GPC)

A number average molecular weight (Mn) and a distribution of molecular weight were measured by GPC. A subject for analysis such as a block copolymer or macro initiator of Example or Comparative Example was put into 5 ml vial, and diluted with tetrahydro furan (THF) to have a concentration of about 1 mg/mL. Afterward, a standard sample for Calibration and a sample for analysis were measured after passing through a syringe filter (pore size: 0.45 μm). As an analysis program, ChemStation produced by Agilent technologies was used, and an elution time for the sample was compared with a calibration curve, thereby obtaining a weight average molecular weight (Mw) and a number average molecular weight (Mn), and a ratio (Mw/Mn) was used to calculate a polydispersity index (PDI). Conditions for measuring GPC are as follows.

<Conditions for Measuring GPC>
Device: 1200 series produced by Agilent technologies
Column: Two PLgel mixed B produced by Polymer laboratories
Solvent: THF
Column temperature: 35° C.
Sample concentration: 1 mg/mL, 200 L injection
Standard sample: Polystyrene (Mp: 3900000, 723000, 316500, 52200, 31400, 7200, 3940, 485)

3. GISAXS (Grazing Incidence Small Angle X Ray Scattering)

The GISAXS analysis was performed in a 3C beam line of the Pohang Light Source. A coating solution was prepared by dissolving a block copolymer to be evaluated in fluorobenzene so as for a solid content to be 0.7 weight %, the coating solution was spin coated on a substrate so as to having a thickness of about 5 nm. The coating area was controlled to be about 2.25 $cm^2$ (coated area: width=1.5 cm, length=1.5 cm). The coated layer was dried for about 1 hour at the room temperature and then subjected to the thermal annealing at about 160° C. for about 1 hour so as for the phase separation structure to be realized. Therefore, the layer in which the phase separation structure was realized was formed. The formed layer was irradiated with X ray so as for an incident angle to be from about 0.12 degrees to 0.23 degrees, which corresponded to an angle between a critical angle of the layer and a critical angle of the substrate, and then the X ray diffraction pattern scattered from the layer was obtained by using a 2D marCCD. At this time, a distance from the layer to the detector was selected so as for the self assembled pattern in the layer to be effectively observed within a range from about 2 m to 3 m. As the substrate, a substrate (a silicone substrate that was treated with piranha solution and that has a wetting angle of about 5 degrees with respect to purified water at the room temperature) having the hydrophilic surface or a substrate (a silicone substrate that was treated with HMDS (hexamethyldisilazane) and that has a wetting angle of about 60 degrees with respect to purified water at the room temperature) having the hydrophobic surface was used.

4. Method for XRD Analysis

XRD analysis was performed by measuring a scattering intensity according to a scattering vector (q) by irradiating a sample with an X ray using a Pohang light source 4C beam line. As a sample, a powder-type block copolymer was obtained by purifying a synthesized block copolymer without specific pretreatment and drying the block copolymer in a vacuum oven for about one day, and put into a cell for XRD measurement. In XRD pattern analysis, an X ray having a vertical size of 0.023 mm and a horizontal size of 0.3 mm was used, and a 2D marCCD was used as a detector. A 2D diffraction pattern obtained by scattering was obtained an image. Information such as a scattering vector and a FWHM were obtained by analyzing the obtained diffraction pattern by numerical analysis method using the least square method. For the analysis, an origin program was applied, a part showing the least intensity in an XRD diffraction pattern was set as a baseline to make the intensity 0, a profile of the XRD pattern peak was fitted by Gaussian fitting, and the scattering vector and the FWHM was obtained from the fitted result. In the Gauss fitting, the R square was set to at least 0.96 or more.

5. Measurement of Surface Energy

Surface energy was measured using a drop-shape analyzer (DSA100, KRUSS). A coating solution was prepared by diluting a material for detection (polymer) with fluorobenzene at a solid content concentration of about 2 wt %, and the prepared coating solution was applied on a silicon wafer by spin coating to have a thickness of about 50 nm and a coating area of 4 cm$^2$ (width: 2 cm, length: 2 cm). The coating layer was dried at room temperature for about 1 hour, and then thermal-annealed at about 160° C. for about 1 hour. Deionized water having a known surface tension was dropped on the film undergoing the thermal annealing, and a mean value of five contact angles obtained by repeating measurement of contact angles five times. Likewise, diiodomethane having a known surface tension was dropped on the film undergoing the thermal annealing, and a mean value of five contact angles obtained by repeating measurement of contact angles five times. Surface energy was obtained by substituting a Strom value with respect to the surface tension of the solvent through the Owens-Wendt-Rabel-Kaelble method using the obtained mean values of the contact angles for the deionized water and diiodomethane. The value of surface energy for each block of the block copolymer was obtained by the above-described method applied to a homopolymer prepared only using a monomer for forming the block.

6. GIWAXS (Grazing Incidence Wide Angle X Ray Scattering)

The GIWAXS analysis was performed in a 3C beam line of the Pohang Light Source. A coating solution was prepared by dissolving a copolymer to be evaluated in toluene so as for a solid content to be 1 weight %, the coating solution was spin coated on a substrate so as to having a thickness of about 30 nm. The coating area was controlled to be about 2.25 cm$^2$ (coated area: width=1.5 cm, length=1.5 cm). The coated layer was dried for about 1 hour at the room temperature and then subjected to the thermal annealing at about 160° C. for about 1 hour so as to form a layer. The formed layer was irradiated with X ray so as for an incident angle to be from about 0.12 degrees to 0.23 degrees, which corresponded to an angle between a critical angle of the layer and a critical angle of the substrate, and then the X ray diffraction pattern scattered from the layer was obtained by using a 2D marCCD. At this time, a distance from the layer to the detector was selected so as for the crystal or liquid crystal structure in the layer to be effectively observed within a range from about 0.1 m to 0.5 m. As the substrate, a silicone substrate that was treated with piranha solution and that has a wetting angle of about 5 degrees with respect to purified water at the room temperature was used.

Scattering intensity at an azimuthal angle from −90 degrees to 90 degrees (an azimuthal angle when an upper direction (out of plane diffraction pattern) is set to be 0 degree) in diffraction pattern from 12 nm$^{-1}$ to 16 nm$^{-1}$ in the GIWAXS was plotted and a full width at half maximum (FWHM) was obtained from the graph via the Gauss fitting. In a case where only a half of a peak during the Gauss fitting was observed, a value twice as much as the obtained FWHM was designated as the FWHM.

7. DSC Analysis

The DSC analysis was performed by using PerkinElmer DSC800 device. It was performed by obtaining an endothermic curve by heating the sample to be analyzed from 25° C. to 200° C. at a heating speed of 10° C. per a minute, then cooling it from 200° C. to −80° C. at a cooling speed of −10° C. per a minute and then heating it from −80° C. to 200° C. at a heating speed of 10° C. per a minute under nitrogen atmosphere by using the device. By analyzing the obtained endothermic curve, a temperature (the melting transition temperature, Tm) at which the melting transition peak was observed was obtained and an area of the peak was calculated. The temperature corresponding to a summit of the peak was selected. A mass per unit area of each peak was obtained by dividing an area of each peak by a mass of the sample and the above calculation can be performed by a program provided in the DSC device.

8 Measurement of the X in the Formula A

The variables D, M, K and L applied in the formula A can be obtained as below.

The D value can be obtained by putting a sample to be measured (a homopolymer prepared only by monomers forming the first block or a homopolymer prepared only by monomers forming the second block) in solvent (ethanol) of which mass and density in air are known and then density of each block can be obtained via its mass and calculating their ratio.

Further, the M value can be obtained from a ratio of molar masses of monomers forming each block of the block copolymer. For example, in a case of each block copolymer in Examples, since the molar mass of the monomer forming the first block in Preparation Example 1 as described below is 346.5 g/mol and the molar mass of the pentafluorostyrene forming the second block is 194.1 g/mol and therefrom the M can be calculated as about 1.79 from their ratio.

Further, the L can be obtained from molar number of hydrogen atom of monomers forming each block of the block copolymer. For example, in a case of each block copolymer in Examples, since the molar number of the hydrogen atom of the monomer forming the first block in Preparation Example 1 as described below is 34 and the molar number of the hydrogen atom in the pentafluorostyrene forming the second block is 3 and therefrom the L can be calculated as about 11.3 from their ratio.

Finally, the K can be calculated from an area of spectrum obtained from the NMR method as described above. In a case where a peak due to one block of the block copolymer is not overlapped with a peak due to the other block of the block copolymer, an area of each peak due to each block can be simply obtained and the K can be obtained from their ratio.

Figure 14:
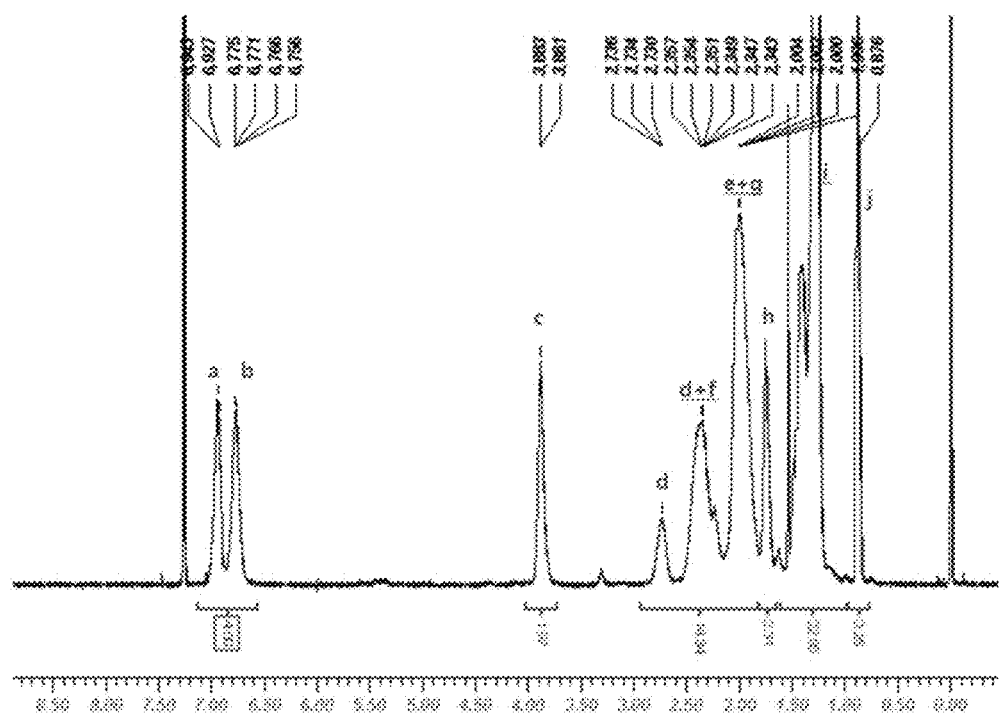
FIG. 14 show an illustrate process during which the K value in the Formula A is calculated.
Figure 15:
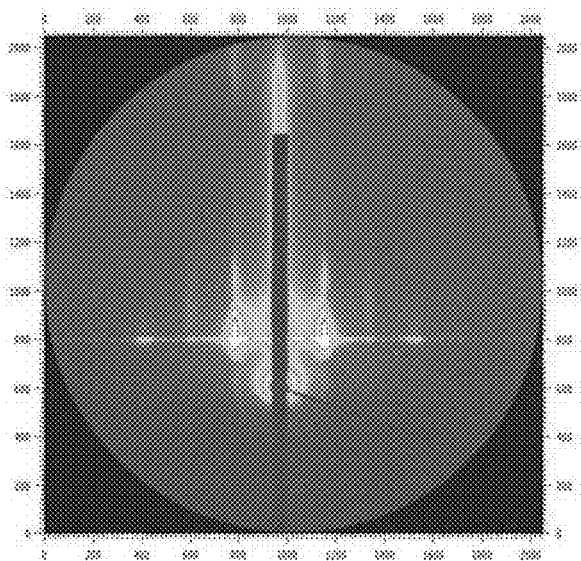
FIGS. 15 to 17 are drawings of GISAXS diffraction patterns.SAXS diffraction patterns.
Figure 16:
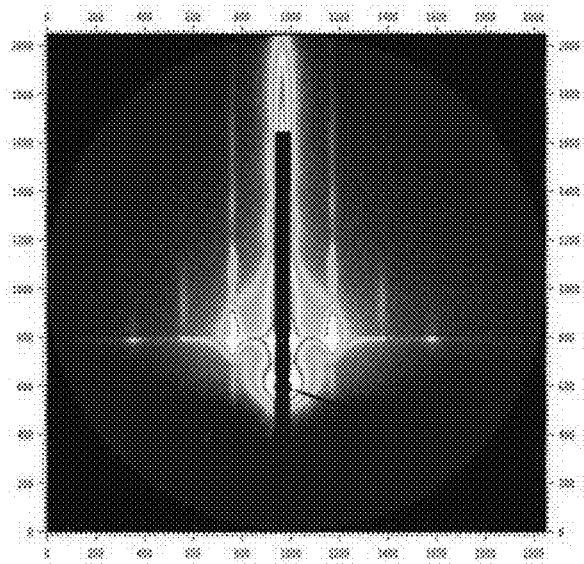
Figure 17:
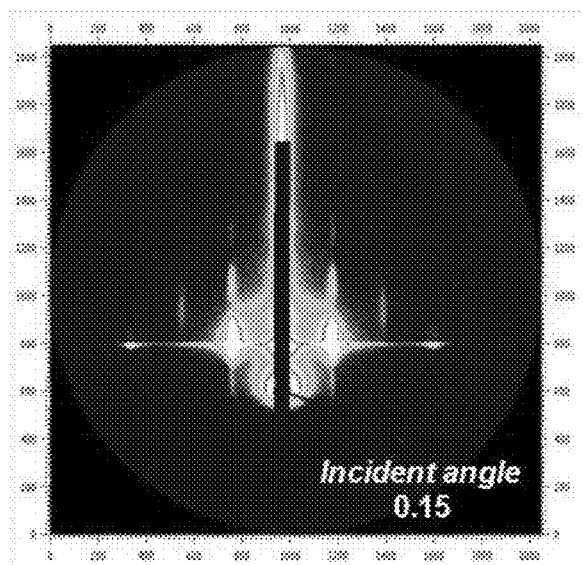

However, in a case where a peak due to one block of the block copolymer is overlapped with a peak due to the other block of the block copolymer, the K should be calculated with considering the above. For example, FIG. 14 is an illustrative NMR spectrum of the block copolymer that was applied in the below Example and Comparative Example and that includes a unit derived from the compound of chemical formula A in Preparation Example 1 and a unit derived from pentafluorostyrene. The portions represented by the "e" and "d" are peaks derived from the second block, i.e., the unit derived from the pentafluorostyrene and other portions represented by the "a," "b," "c," "f," "g," "h," "i" and "j" are peaks derived from the unit derived from the compound of chemical formula A in Preparation Example 1. As can be confirmed from the drawing, the peaks represented by the "e" and "g" are overlapped with the peaks represented by the "d" and "f," and, in this case, the K should be obtained considering the overlapped portions.

The method for obtaining the K with considering the overlapped portions is known, and, for example, it can be obtained by using a NMR analysis program such as Mest-ReC.

Preparation Example 1. Synthesis of Monomer (A)

A compound of Formula A (DPM-C12) was synthesized by the following method. Hydroquinone (10.0 g, 94.2 mmol) and 1-bromododecane (23.5 g, 94.2 mmol) were put into a 250 mL flask, dissolved in 100 mL acetonitrile, treated with an excessive amount of potassium carbonate to allow a reaction at 75° C. for about 48 hours under a nitrogen condition. After the reaction, remaining potassium carbonate was filtered to remove, and the acetonitrile used in the reaction was also removed. Here, a mixed solvent of dichloromethane (DCM) and water was added to work up, and a separated organic layer was dehydrated with MgSO₄. Therefore, a white solid product (4-dodecyloxyphenol; 9.8 g, 35.2 mmol) was obtained with an yield of about 37% through column chromatography using DCM.
<NMR Analysis Result>
¹H-NMR(CDCl₃): δ6.77 (dd, 4H); δ4.45 (s, 1H); δ3.89 (t, 2H); δ1.75 (p, 2H); δ1.43 (p, 2H); δ1.33-1.26 (m, 16H); δ0.88 (t, 3H).

Synthesized 4-dodecyloxyphenol (9.8 g, 35.2 mmol), methacrylic acid (6.0 g, 69.7 mmol), dicyclohexylcarbodiimide (DCC; 10.8 g, 52.3 mmol) and p-dimethylaminopyridine (DMAP; 1.7 g, 13.9 mmol) were put into a flask, and treated with 120 mL of methylenechloride to allow a reaction at room temperature for 24 hours under nitrogen. After the reaction was completed, a salt produced in the reaction (urea salt) was removed using a filter, and remaining methylenechloride was also removed. Debris was removed through column chromatography using hexane and dichloromethane (DCM) as moving phases, and then a product thereby was recrystallized in a mixed solvent of methanol and water (1:1 mixture), thereby obtaining a white solid product (7.7 g, 22.2 mmol) with an yield of 63%.
<NMR Analysis Result>
¹H-NMR(CDCl₃): δ7.02 (dd, 2H); δ6.89 (dd, 2H); δ6.32 (dt, 1H); δ5.73 (dt, 1H); δ3.94 (t, 2H); δ2.05 (dd, 3H); δ1.76 (p, 2H); δ1.43 (p, 2H); 1.34-1.27 (m, 16H); δ0.88 (t, 3H).

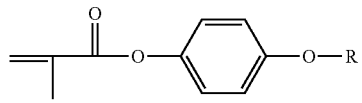

[Formula A]

In Formula A, R is a linear alkyl group having 12 carbon atoms.

Preparation Example 2. Synthesis of Monomer (G)

A compound of Formula G was synthesized by the method according to Preparation Example 1, except that 1-bromobutane, instead of 1-bromododecane, was used. The NMR analysis result for the compound is shown below.
<NMR Analysis Result>
¹H-NMR(CDCl₃): δ7.02 (dd, 2H); δ6.89 (dd, 2H); δ6.33 (dt, 1H); δ5.73 (dt, 1H); δ3.95 (t, 2H); δ2.06 (dd, 3H); δ1.76 (p, 2H); δ1.49 (p, 2H); δ0.98 (t, 3H).

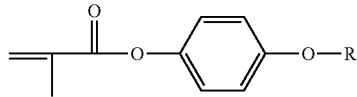

[Formula G]

In Formula B, R is a linear alkyl group having 8 carbon atoms.

Preparation Example 3. Synthesis of Monomer (D)

A compound of Formula D was synthesized by the method according to Preparation Example 1, except that 1-bromotetradecane, instead of 1-bromododecane, was used. The NMR analysis result for the compound is shown below.
<NMR Analysis Result>
¹H-NMR(CDCl₃): δ7.02 (dd, 2H); δ6.89 (dd, 2H); δ6.33 (dt, 1H); δ5.73 (dt, 1H); δ3.94 (t, 2H); δ2.05 (dd, 3H); δ1.77 (p, 2H); δ1.45 (p, 2H); 1.36-1.27 (m, 20H); δ0.88 (t, 3H.)

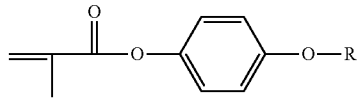

[Formula D]

In Formula D, R is a linear alkyl group having 14 carbon atoms.

Preparation Example 4. Synthesis of Monomer (E)

A compound of Formula E was synthesized by the method according to Preparation Example 1, except that 1-bromohexadetane, instead of 1-bromododecane, was used. The NMR analysis result for the compound is shown below.
<NMR Analysis Result>
¹H-NMR(CDCl₃): δ7.01 (dd, 2H); δ6.88 (dd, 2H); δ6.32 (dt, 1H); δ5.73 (dt, 1H); δ3.94 (1, 2H); δ2.05 (dd, 3H); δ1.77 (p, 2H); δ1.45 (p, 2H); 1.36-1.26 (m, 24H); δ0.89 (1, 3H)

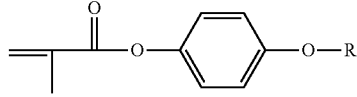

[Formula E]

In Formula E, R is a linear alkyl group having 16 carbon atoms.

Results of GIWAXS and DSC Analysis

The result of the GIWAXS and DSC analysis performed with respect to 4 homopolymers were prepared by using monomers in Preparation Examples 1 to 4 is stated in Table 1 below. The homopolymers were prepared by the same method as that for preparing the macroinitiator described in the Example and Comparative Example below. Further, the result of the GIWAXS analysis with respect to each homopolymer is shown in FIGS. 10 to 13. FIGS. 10 to 13 show the result of the GIWAXS of homopolymers prepared by monomers in Preparation Examples 1 to 4 respectively.

Figure 10:
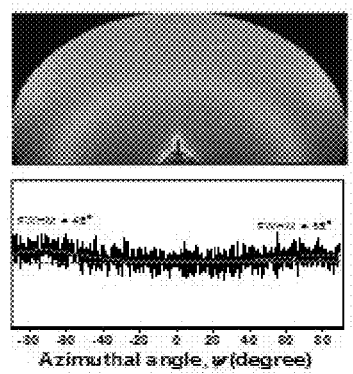
FIGS. 10 to 13 are drawings showing results of GIWAXS.
Figure 12:
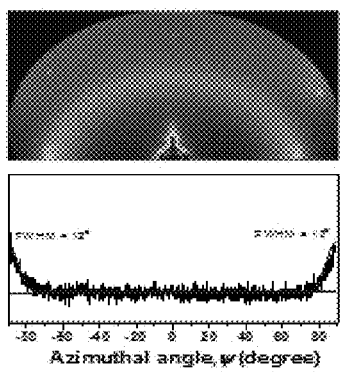
Figure 13:
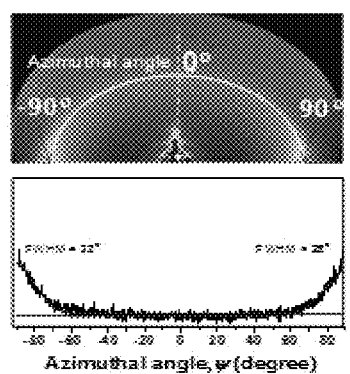

The R square of the Gauss fitting in FIG. 10 was about 0.264, the R square of the Gauss fitting in FIG. 12 was about 0.676 and the R square of the Gauss fitting in FIG. 13 was about 0.932.

TABLE 1

| | Preparation Example | | | |
|---|---|---|---|---|
| | 1 | 2 | 3 | 4 |
| Tg | — | 33 | — | — |
| Tm | −3 | — | 23 | 46 |
| Ti | 15 | — | 60 | 60 |
| M/I | 3.67 | — | 5.75 | 71.86 |
| FWHM1 | 48 | — | 13 | 23 |
| FWHM2 | 58 | — | 12 | 26 |
| Chain-forming atoms | 12 | 4 | 14 | 16 |

Tg: glass transition temperature (° C.)
Tm: melting transition temperature (° C.)
Ti: isotropic transition temperature (° C.)
M/I: a ratio of an area (M) of the melting transition peak relative to an area (I) of the isotropic transition peak
FWHM1: a full width at half maximum (unit: degrees) at an azimuthal angle from −90 to −70 degrees
FWHM2: a full width at half maximum (unit: degrees) at an azimuthal angle from 70 to 90 degrees
Chain-forming atoms: a number of the chain-forming atoms in the first block (= the number of carbon atoms in the "R" of the chemical formula in each Preparation Example)

Example 1

Figure 2:
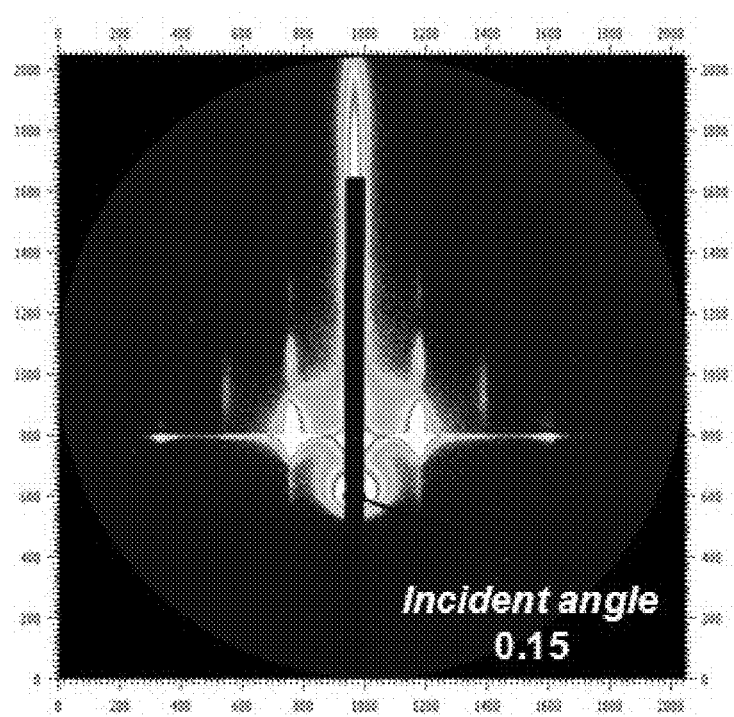

1.785 g of the monomer (A) of Preparation Example 1, 38 mg of a reversible addition-fragmentation chain transfer (RAFT) reagent, cyanoisopropyldithiobenzoate, 14 mg of a radical initiator, azobisisobutyronitrile (AIBN), and 4.765 ml of benzene were put into a 10 mL Schlenk flask, and stirred at room temperature for 30 minutes under a nitrogen atmosphere to allow an RAFT polymerization reaction at 70° C. for 4 hours. After the polymerization, a reaction solution was precipitated in 250 ml of methanol as an extraction solvent, and dried through decreased pressure filtration, thereby preparing a pink macroinitiator. The yield of the macroinitiator was about 83.1 weight %, and the number average molecular weight (Mn) and distribution of molecular weight (Mw/Mn) of the macroinitiator were 11,400 and 1.15, respectively. 0.3086 g of the macroinitiator, 1.839 g of a pentafluorostyrene monomer and 0.701 ml of benzene were put into a 10 mL Schlenk flask, and stirred at room temperature for 30 minutes under a nitrogen atmosphere to allow an RAFT polymerization reaction at 115° C. for 4 hours. After the polymerization, a reaction solution was precipitated in 250 ml of methanol as an extraction solvent, and dried through decreased pressure filtration, thereby preparing a light pink block copolymer. The yield of the block copolymer was about 27.1 weight %, and the number average molecular weight (Mn) and distribution of molecular weight (Mw/Mn) of the block copolymer were 18,900 and 1.19, respectively. The block copolymer includes a first block derived from the monomer (A) of Preparation Example 1 and a second block derived from the pentafluorostyrene monomer. The result of the GISAXS measuring performed with respect to a surface, as a hydrophilic surface, of which a wetting angle at room temperature was 5 degrees by the method as described above is shown in FIG. 1 and the result of the GISAXS measuring performed with respect to a surface, as a hydrophobic surface, of which a wetting angle at room temperature was 60 degrees by the method as described above is shown in FIG. 2. From FIGS. 1 and 2, it can be confirmed that the in plane phase diffraction patterns can be observed in any case.

Example 2

A block copolymer was prepared using a macroinitiator and a pentafluorostyrene as monomers by the method according to Example 1, except that the monomer (D) of Preparation Example 3, instead of the monomer (A) of Preparation Example 1, was used. The block copolymer includes a first block derived from the monomer (D) of Preparation Example 3 and a second block derived from the pentafluorostyrene monomer. The GISAXS analysis was performed by the same method as in Example 1 and the in plane phase diffraction patterns were confirmed both on the hydrophilic and the hydrophobic surface.

Example 3

A block copolymer was prepared using a macroinitiator and a pentafluorostyrene as monomers by the method according to Example 1, except that the monomer (E) of Preparation Example 4, instead of the monomer (A) of Preparation Example 1, was used. The block copolymer includes a first block derived from the monomer (E) of Preparation Example 4 and a second block derived from the pentafluorostyrene monomer. The GISAXS analysis was performed by the same method as in Example 1 and the in plane phase diffraction patterns were confirmed both on the hydrophilic and the hydrophobic surface.

Comparative Example 1

A block copolymer was prepared using a macroinitiator and a pentafluorostyrene as monomers by the method according to Example 1, except that the monomer (G) of Preparation Example 2, instead of the monomer (A) of Preparation Example 1, was used. The block copolymer includes a first block derived from the monomer (G) of Preparation Example 2 and a second block derived from the pentafluorostyrene monomer. The GISAXS analysis was performed by the same method as in Example 1; however the in plane phase diffraction patterns were not confirmed on the hydrophilic and the hydrophobic surface.

Comparative Example 2

A block copolymer was prepared using a macroinitiator and a pentafluorostyrene as monomers by the method according to Example 1, except that the 4-methoxyphenyl methacrylate, instead of the monomer (A) of Preparation Example 1, was used. The block copolymer includes a first block derived from the 4-methoxyphenyl methacrylate and a second block derived from the pentafluorostyrene monomer. The GISAXS analysis was performed by the same method as in Example 1; however the in plane phase diffraction patterns were not confirmed on the hydrophilic and the hydrophobic surface.

Comparative Example 3

A block copolymer was prepared using a macroinitiator and a pentafluorostyrene as monomers by the method according to Example 1, except that the dodecyl methacrylate, instead of the monomer (A) of Preparation Example 1, was used. The block copolymer includes a first block derived from the dodecyl methacrylate and a second block derived from the pentafluorostyrene monomer. The GISAXS analysis was performed by the same method as in Example 1; however the in plane phase diffraction patterns were not confirmed on the hydrophilic and the hydrophobic surface.

GPC results for the macroinitiators and the block copolymers prepared in the above Preparation Examples are summarized and listed in Table 2.

TABLE 2

|  |  | Example | | | Comparative Example | | |
|---|---|---|---|---|---|---|---|
|  |  | 1 | 2 | 3 | 1 | 2 | 3 |
| MI | Mn | 11400 | 8700 | 9400 | 9000 | 7800 | 8000 |
|  | PDI | 1.15 | 1.18 | 1.15 | 1.17 | 1.13 | 1.16 |
| BCP | Mn | 18900 | 17400 | 18900 | 18800 | 18700 | 16700 |
|  | PDI | 1.19 | 1.18 | 1.17 | 1.20 | 1.16 | 1.20 |

MI: macroinitiator
BCP: block copolymer
Mn: number average molecular weight
PDI: polydispersity index The result of evaluating properties of each block copolymer is stated in Table 3 below.

TABLE 3

|  |  | Example | | | Comparative Example | | | Ref |
|---|---|---|---|---|---|---|---|---|
|  |  | 1 | 2 | 3 | 1 | 2 | 3 |  |
| The first | SE | 30.83 | 26.924 | 27.79 | 37.37 | 48.95 | 19.1 | 38.3 |
| Block | De | 1 | 0.99 | 1.00 | 1.11 | 1.19 | 0.93 | 1.05 |
| The second | SE | 24.4 | 24.4 | 24.4 | 24.4 | 24.4 | 24.4 | 41.8 |
| block | De | 1.57 | 1.57 | 1.57 | 1.57 | 1.57 | 1.57 | 1.18 |
| SE difference |  | 6.43 | 2.524 | 3.39 | 12.98 | 24.55 | 5.3 | 3.5 |
| De difference |  | 0.57 | 0.58 | 0.57 | 0.46 | 0.38 | 0.64 | 0.13 |
| Chain forming atom |  | 12 | 14 | 16 | 4 | 1 | 12 | — |
| n/D |  | 3.75 | 4.24 | 4.44 | 2.82 | 1.98 | — | — |

SE: the surface energy (unit: mN/m)
De: density (g/cm$^3$)
SE difference: an absolute value of a difference between the surface energies of the first and second block
De difference: an absolute value of a difference between the densities of the first and second block
n/D: the value calculated by the Equation 2 (nq/(2 × π)) (n is the number of chain-forming atoms of the side chain, q is the scattering vector (q) showing the peak having the largest peak area within scattering vector range from 0.5 nm$^{-1}$ to 10 nm$^{-1}$.
Ref.: polystyrene-polymethylmethacrylate block copolymer (the first block: polystyrene block, the second block: polymethylmethacrylate block)

Results for analyzing XRD patterns for the macroinitiator used for preparing each block copolymer by the above-described methods are summarized and listed in Table 4. In a case of the Comparative Example 3, no peak was observed within a range of scattering vectors from 0.5 nm$^{-1}$ to 10 nm$^{-1}$.

TABLE 2

|  | Example | | | Comparative Example | | |
|---|---|---|---|---|---|---|
|  | 1 | 2 | 3 | 1 | 2 | 3 |
| q peak value(unit: nm$^{-1}$) | 1.96 | 1.83 | 1.72 | 4.42 | 3.18 | — |
| FWHM (unit: nm$^{-1}$) | 0.57 | 0.45 | 0.53 | 0.97 | 1.06 | — |

Experiment Example 1. Evaluation of Self Assembling Properties

Figure 3:
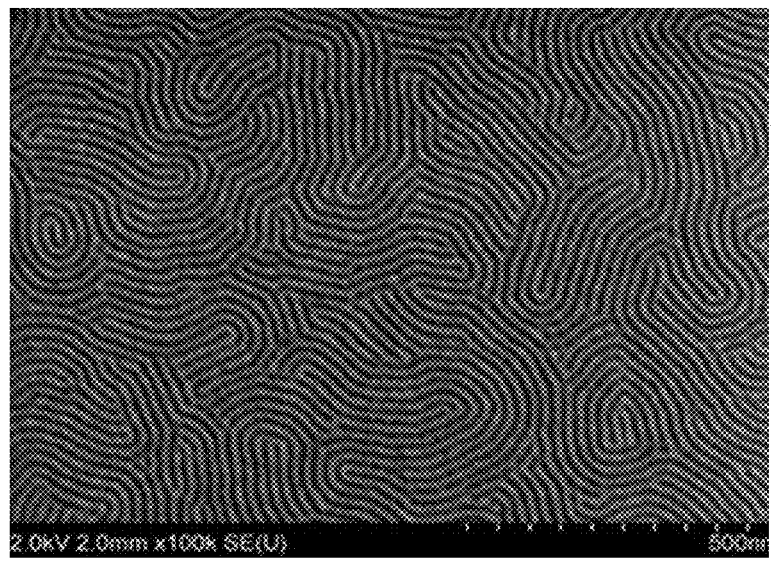
FIGS. 3 to 9 show SEM images of polymer layers.
Figure 4:
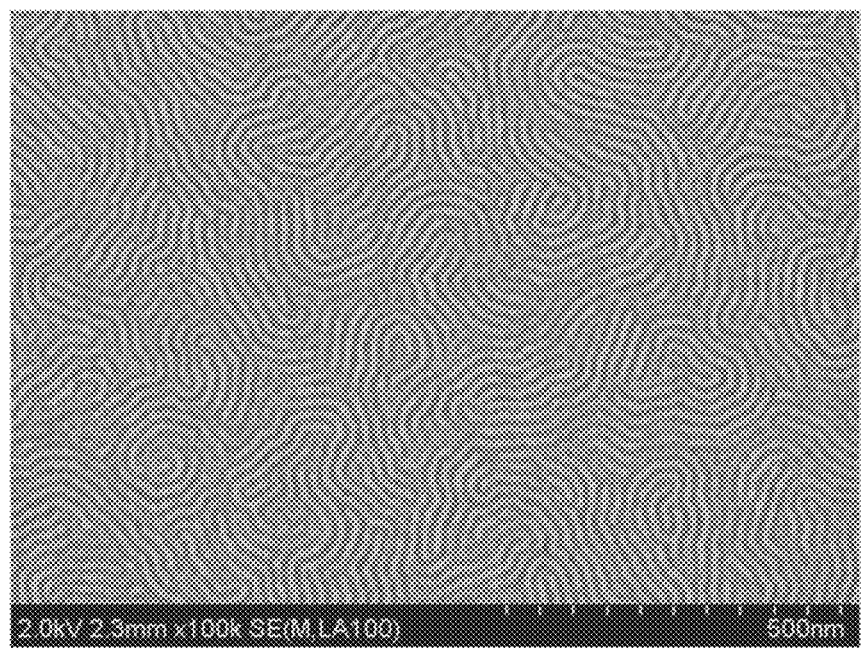
Figure 5:
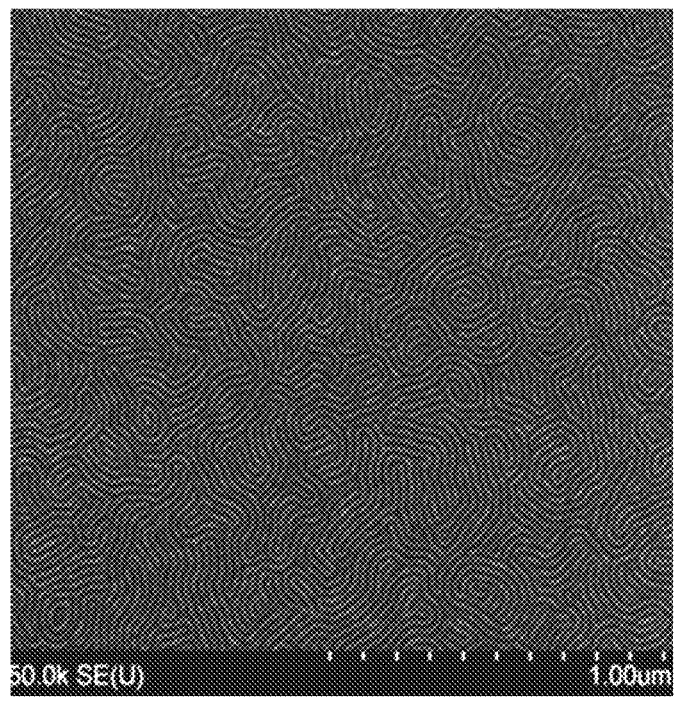
Figure 6:
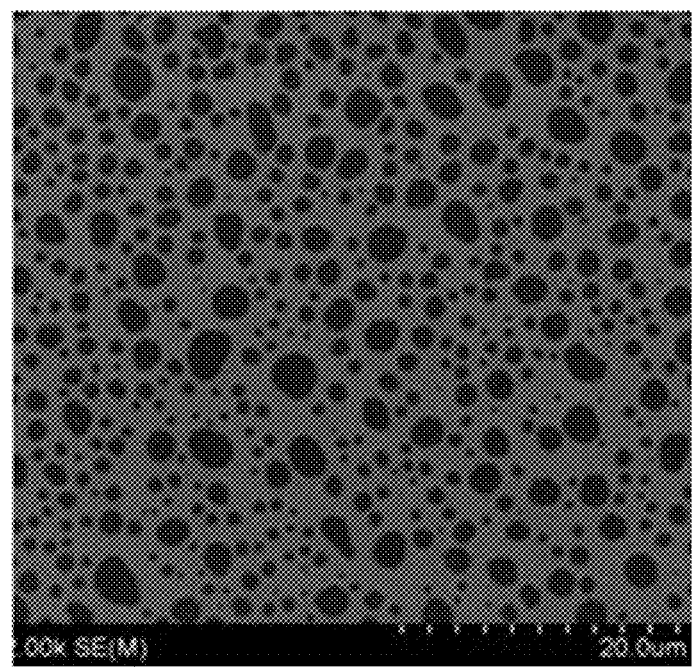

A coating solution prepared by diluting the block copolymer of Examples or Comparative Examples in fluorobenzene so as to have 0.7 weight % of solid content was spin coated on a silicon wafer (coating area: width×length=1.5 cm×1.5 cm) so as to have a thickness of about 5 nm, the coated coating solution was dried under a room temperature for about an hour and then was subjected to a thermal annealing at 160° C. for about an hour so as to form a self assembled layer. The SEM (Scanning Electron Microscope) analysis was performed to each of the formed layers. FIGS. 3 to 5 are the SEM images of the layers formed by the block copolymers of Examples 1 to 3. As confirmed from the figures, in a case of the block copolymer, a polymer layer that was self assembled in a line shape was effectively formed. However, in a case of Comparative Example, an appropriate phase separation was not realized. For example, FIG. 6 is a SEM result of Comparative Example 3 and it can be confirmed that an effective phase separation was not realized.

Experiment Example 2. Evaluation of Self Assembling Properties

Figure 7:
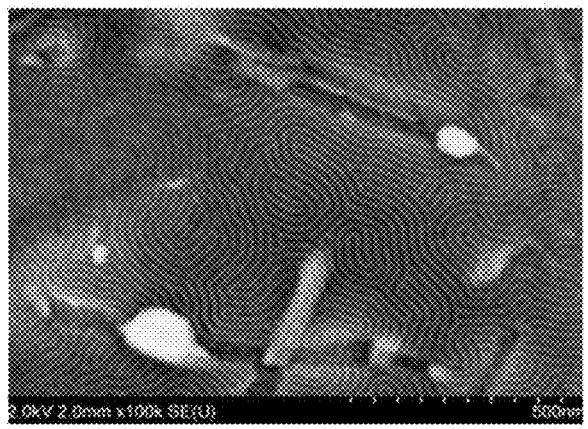
Figure 8:
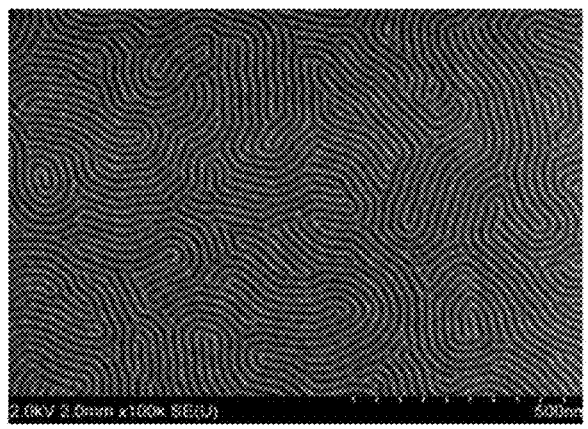
Figure 9:
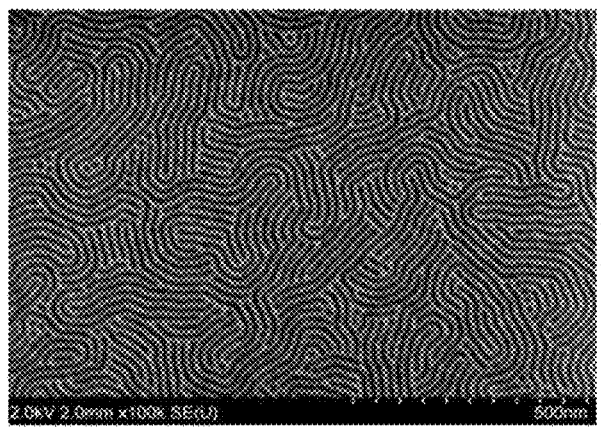

By using the block copolymer in Example 1, a polymer layer was formed by the same method as in the Experiment Example 1. The polymer layer was formed on a silicon substrate which was treated with piranha solution and of which a wetting angle at room temperature was 5 degrees; on a silicon oxide substrate of which a wetting angle at room temperature was 45 degrees or on a silicon substrate which was treated with HMDS (hexamethyldisilazane) and of which a wetting angle at room temperature was 60 degrees. FIGS. 7 to 9 are SEM images of polymer layers formed on the surfaces of which the wetting angles were 5 degrees, 45 degrees and 60 degrees respectively. From them, it can be confirmed that the block copolymer can form effective phase separation structure regardless of surface property of the substrate.

Experiment Example 3

Block copolymers (BCP1 to BCP4) were prepared by the same method as in Example 1, except that the X value in Formula A could be changed as below by controlling the molar ratio of the macroinitiator and monomer.

TABLE 5

| | The X in formula A | D | M | K | L |
|---|---|---|---|---|---|
| BCP1 | 2.18 | 1.57 | 1.79 | 0.21 | 11.3 |
| BCP2 | 1.85 | 1.57 | 1.79 | 0.29 | 11.3 |
| BCP3 | 1.75 | 1.57 | 1.79 | 0.33 | 11.3 |
| BCP4 | 1.26 | 1.57 | 1.79 | 0.95 | 11.3 |

Figure 11:
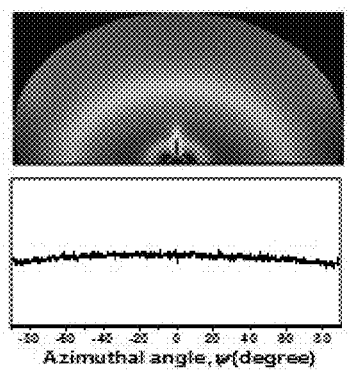

D: a ratio (D2/D1) of a density (D2) of the second block relative to a density (D1) of the first block
M: a ratio (M1/M2) of a molar mass (346.5 g/mol, M1) of the monomer of the chemical formula A of Preparation Example 1 forming the first block relative to a molar mass (194.1 g/mol, M2) of the pentafluorostyrene forming the second block
K: a ratio (A2/A1) of an area (A2) of a peak exhibited due to the second block in $^1$H-NMR relative to an area (A1) of a peak exhibited due to the first block in $^1$H-NMR
L: a ratio (H1/H2) of a molar number (34, H1) of hydrogen atom in the monomer of the chemical formula A of Preparation Example 1 forming the first block relative to a molar number (3, H2) of hydrogen atom in the pentafluorostyrene forming the second block A coating solution prepared by diluting each of the above block copolymers in fluorobenzene so as to have 0.7 weight % of solid content was spin coated on a silicon wafer (coating area: width×length=1.5 cm×1.5 cm) so as to have a thickness of about 5 nm, the coated coating solution was dried under a room temperature for about an hour and then was subjected to a thermal annealing at 160° C. for about an hour so as to form a polymer layer. The GISAXS analysis was performed to the formed layer and the results are shown in drawings. FIGS. 10 to 12 are the results of BCP1, BCP2 and BCP3. From the drawings, it can be confirmed that the block copolymer can exhibit the in plane diffraction pattern on the GISAXS however, in a case of BCP4, a clear result cannot be confirmed.

What is claimed is:

1. A block copolymer comprising a first block and a second block different from the first block,
   wherein the first block comprises a linear or branched side chain of which a number of chain-forming atoms is 8 or more, wherein the number of chain forming atoms is a number of atoms constituting the longest linear structure in the side chain,
   and wherein the first block exhibits peaks having a full width at half maximum of 5 degrees to 70 degrees at an azimuth angle ranging from −90 to −70 degrees and at an azimuth angle ranging from 70 to 90 degrees of a diffraction pattern of scattering vectors ranging from 12 nm$^{-1}$ to 16 nm$^{-1}$ in a grazing incidence wide angle X-ray scattering (GIWAXS) spectrum and wherein the azimuth angle is an angle when an out of plane diffraction pattern of the GIWAXS spectrum is set to be 0 degree.

2. The block copolymer of claim 1, wherein the block copolymer exhibits a melting transition peak or an isotropic transition peak within a range from −80° C. to 200° C.

3. The block copolymer of claim 2, wherein the block copolymer exhibits both of the melting transition peak and the isotropic transition peak.

4. The block copolymer of claim 3, wherein a difference (Ti−Tm) between a temperature (Ti) at which the isotropic transition peak is shown and a temperature (Tm) at which the melting transition peak is shown is from 5° C. to 70° C.

5. The block copolymer of claim 3, wherein a ratio (M/I) of an area (M) of the melting transition peak relative to an area (I) of the isotropic transition peak is from 0.1 to 500.

6. The block copolymer of claim 2, wherein the melting transition peak is exhibited within a range from −10° C. to 55° C.

7. The block copolymer of claim 2, wherein the first block comprises a side chain satisfying the Equation 1:

$$10° \text{ C.} \leq Tm - 12.25° \text{ C.} \times n + 149.5° \text{ C.} \leq 10° \text{ C.} \quad \text{[Equation 1]}$$

wherein Tm is a temperature at which the melting transition peak is shown and n is the number of chain-forming atoms of the side chain.

8. The block copolymer of claim 1, wherein an absolute value of a difference in surface energy between the first block and the second block is 10 mN/m or less.

9. The block copolymer of claim 1, wherein the first or second block comprises an aromatic structure.

10. The block copolymer of claim 1, wherein the first block and the second block comprise an aromatic structure.

11. The block copolymer of claim 1, wherein the first block comprises an aromatic structure that does not have halogen atoms and the second block comprises an aromatic structure having halogen atom(s).

12. The block copolymer of claim 1, wherein the first or second block comprises halogen atom.

13. The block copolymer of claim 1, wherein the second block comprises halogen atom(s).

14. The block copolymer of claim 1, wherein the first or second block comprises an aromatic structure to which the side chain is linked.

15. The block copolymer of claim 14, wherein the side chain is linked to the aromatic structure via an oxygen atom or a nitrogen atom.

16. The block copolymer of claim 1, wherein the first or second block comprises an aromatic structure substituted with halogen atom(s).

17. The block copolymer of claim 1, wherein the first block comprises an aromatic structure to which the side chain is linked and the second block comprises an aromatic structure substituted with halogen atom(s).

18. The block copolymer of claim 1, wherein the first block comprises a cyclic structure and the side chain is linked to the cyclic structure.

19. The block copolymer of claim 18, wherein the cyclic structure does not comprise halogen atoms.

20. The block copolymer of claim 1, wherein the second block comprises at least 3 halogen atoms.

21. The block copolymer of claim 20, wherein the second block comprises a cyclic structure substituted with halogen atoms.

22. The block copolymer of claim 1, wherein the first block comprises a unit represented by Formula 1 below:

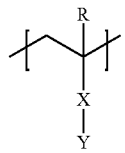

[Formula 1]

wherein, R is a hydrogen or an alkyl group having 1 to 4 carbon atom(s), X is a single bond, an oxygen atom, a sulfur atom, —S(=O)$_2$—, a carbonyl group, an alkylene group, an alkenylene group, an alkynylene group, —C(=O)—X$_1$— or —X$_1$—C(=O)—, where the X$_1$ is an oxygen atom, a sulfur atom, —S(=O)$_2$—, an alkylene group, an alkenylene group or an alkynylene group, and Y is a monovalent substituent including a ring structure to which the side chain is linked.

23. The block copolymer of claim 1, wherein the second block comprises a unit represented by Formula 3 below:

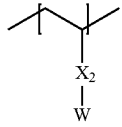

[Formula 3]

wherein the $X_2$ is a single bond, an oxygen atom, a sulfur atom, —S(=O)$_2$—, an alkylene group, an alkenylene group, an alkynylene group, —C(=O)—X$_1$— or —X$_1$—C(=O)—, where the $X_1$ is a single bond, an oxygen atom, a sulfur atom, —S(=O)$_2$—, an alkylene group, an alkenylene group or an alkynylene group, and the W is an aryl group including at least one halogen atom.

24. A polymer layer including the block copolymer of claim 1, wherein the block copolymer is self-assembled.

25. A process for preparing a polymer layer, including forming a polymer layer including the block copolymer of claim 1 on a substrate, wherein the block copolymer is self-assembled.

26. A pattern forming method including selectively eliminating the first or second block from the block copolymer of claim 1, wherein the block copolymer is self-assembled in a polymer layer, wherein the polymer layer is on a substrate.

* * * * *